US011352635B2

(12) United States Patent
Sayre et al.

(10) Patent No.: US 11,352,635 B2
(45) Date of Patent: Jun. 7, 2022

(54) **SYSTEMS AND METHODS FOR ENHANCING TRICHOME FORMATION AND DENSITY IN *CANNABIS***

(71) Applicant: TRAIT BIOSCIENCES, INC., Los Alamos, NM (US)

(72) Inventors: Richard Sayre, Los Alamos, NM (US); Maria Soto-Aguilar, Los Alamos, NM (US); Tawanda Zidenga, Los Alamos, NM (US); Elton Carvalho Goncalves, Los Alamos, NM (US)

(73) Assignee: TRAIT BIOSCIENCES, INC., Los Alamos, NM (US)

( * ) Notice: Subject to any disclaimer, the term of this patent is extended or adjusted under 35 U.S.C. 154(b) by 210 days.

(21) Appl. No.: 16/929,679

(22) Filed: Jul. 15, 2020

(65) Prior Publication Data

US 2021/0032650 A1 Feb. 4, 2021

Related U.S. Application Data

(63) Continuation of application No. 16/515,377, filed on Jul. 18, 2019, now Pat. No. 10,724,048, which is a continuation-in-part of application No. PCT/US2019/015039, filed on Jan. 24, 2019.

(60) Provisional application No. 62/621,166, filed on Jan. 24, 2018.

(51) Int. Cl.
*C12N 15/82* (2006.01)

(52) U.S. Cl.
CPC ..... *C12N 15/8262* (2013.01); *C12N 15/8243* (2013.01)

(58) Field of Classification Search
CPC .................................. C12N 15/8262
See application file for complete search history.

(56) References Cited

U.S. PATENT DOCUMENTS

| 10,724,048 | B2 * | 7/2020 | Sayre | ........................ A01H 6/28 |
| 2011/0179526 | A1 | 7/2011 | Molinero et al. | |
| 2019/0119694 | A1 | 4/2019 | Roscow, Jr. | |

FOREIGN PATENT DOCUMENTS

WO 2018176055 A2 9/2018

OTHER PUBLICATIONS

Matias-Hernandez L. et al. The Plant Journal; Feb. 16, 2017, pp. 520-534. (Year: 2017).*
GenBank Accession No. KC118530.1, Artemisia annua cultivar Chongqing MYB transcription factor mRNA, complete eds, Jun. 2, 2014 [online]. [Retrieved on Jul. 8, 2019]. Retrieved from the internet: <URL: https://www.ncbi.nlm.nih.gov/nuccore/KC118530> Entire document.
GenBank Accession No. JW055681.1, TSA: Capsicum annuum MGMT_Contig5437, mRNA sequence, Sep. 1, 2012 [online]. [Retrieved on Jul. 8, 2019], Retrieved from the internet: <URL: https://www.ncbi.nlm.nih.gov/nuccore/JW055681 > Entire document.
International Search Report and Written Opinion dated Aug. 16, 2019 in International Application No. PCT/US19/15039.
MacKinnon, L., Thesis 2003; University of Dundee, 130 pages. (Year: 2003).
Luis Matias-Hernandez et al: AaMYB1 and its orthologue AtMYB61 affect terpene metabolism and trichome development in Artemisia annua and *Arabidopsis thaliana*11 , The Plant Journal, vol. 90, No. 3, Mar. 27, 2017 (Mar. 27, 2017), pp. 520-534, XP055636153, GB ISSN: 0960-7412, DOI: 10.1111/tpj.13509 the whole document.
Christelle M. Andre et al: Cannabi s sativa: The Plant of the Thousand and One Molecules11 , Frontiers in Plant Science, vol. 7, Feb. 4, 2016 (Feb. 4, 2016), pp. 1-17, XP055581704, DOI: 10.3389/fpls.2016.00019; pp. 8-10: 11 Cannabis trichomes: small; factories of phytochemicals11 .; p. 9, left-hand column, line 6—p. 10, left-hand column, line 10 p. 11, left-hand column, paragraph 4.
Alexandre Huchelmann et al: Plant Glandular Trichomes: Natural Cell Factories of High Biotechnological Interest 11 , Plant Physiology, vol. 175, No. 1, Jul. 19, 2017 (Jul. 19, 2017), pp. 6-22, XP055665110, Rockville, MD, USA ISSN: 0032-0889, DOI: 10.1104/pp.17.00727 *abstract*.
European Search Report dated Feb. 20, 2020 in EP Application No. 19187773.7, 7 pages.

* cited by examiner

*Primary Examiner* — Russell Kallis
(74) *Attorney, Agent, or Firm* — Berg Hill Greenleaf & Ruscitti LLP

(57) ABSTRACT

The present invention includes systems, methods and compositions for increasing trichome formation and/or density in cannabinoid producing plants, such as *Cannabis* and hemp. Additional aspects of the invention further include systems, methods and compositions for increasing cannabinoid and terpene biosynthetic and storage capacity in *Cannabis*.

25 Claims, 12 Drawing Sheets

Specification includes a Sequence Listing.

SYSTEMS AND METHODS FOR ENHANCING TRICHOME FORMATION AND DENSITY IN *CANNABIS*

This US Non-Provisional application is a continuation of U.S. patent application Ser. No. 16/515,377, filed Jul. 18, 2019, which is a continuation-in-part of PCT/US2019/015039, filed Jan. 24, 2019, which claims the benefit of and priority to provisional application No. 62/621,166, filed Jan. 24, 2018, the specification and figures of which are incorporated by reference in their entirety.

SEQUENCE LISTING

The instant application contains a Sequence Listing which has been submitted electronically in ASCII format and is hereby incorporated by reference in its entirety. Said ASCII copy, created on Sep. 23, 2020, is named "90425.00340-Sequence-Listing.txt" and is 38 Kbytes in size.

TECHNICAL FIELD

The current inventive technology relates to the field of genetically modified plants. In particular, current inventive technology includes stably transformed cannabinoid producing plaints, such as *Cannabis*. In certain preferred embodiments, the inventive technology includes a novel systems and methods of enhancing trichome formation and density in *Cannabis* and/or hemp.

BACKGROUND

Cannabinoids are a class of specialized compounds synthesized by *Cannabis*. They are formed by condensation of terpene and phenol precursors. As shown in FIG. 1, they include these more abundant forms: Delta-9-tetrahydrocannabinol (THC), cannabidiol (CBD), cannabichromene (CBC), and cannabigerol (CBG). Another cannabinoid, cannabinol (CBN), is formed from THC as a degradation product and can be detected in some plant strains.

Typically, THC, CBD, CBC, and CBG occur together in different ratios in the various plant strains. These cannabinoids are generally lipophilic, nitrogen-free, mostly phenolic compounds and are derived biogenetically from a monoterpene and phenol, the acid cannabinoids from a monoterpene and phenol carboxylic acid, and have a C21 base. Cannabinoids also find their corresponding carboxylic acids in plant products. In general, the carboxylic acids have the function of a biosynthetic precursor. For example, these compounds arise in vivo from the THC carboxylic acids by decarboxylation the tetrahydrocannabinols Δ9- and Δ8-THC and CBD from the associated cannabidiol.

Cannabinoids are classified into two types, neutral cannabinoids and cannabinoid acids, based on whether they contain a carboxyl group or not. It is known that, in fresh plants, the concentrations of neutral cannabinoids are much lower than those of cannabinoid acids. Thus, as generally shown in FIG. 2, THC and CBD may be derived artificially from their acidic precursor compounds tetrahydrocannabinolic acid (THCA) and cannabidiolic acid (CBDA) by non-enzymatic decarboxylation.

As detailed below, efforts to generate *Cannabis* plants that produce and/or accumulate high levels of cannabinoids have raised a number of technical problems. Chief among them is the fact that cannabinoid synthesis produces toxic by-products. Notably, both CBDA and THCA synthases require molecular oxygen, in conjunction with a molecule of FAD, to oxidize Cannabigerolic acid (CBGA). Specifically, as shown in FIG. 3, two electrons from the substrate are accepted by an enzyme-bound FAD, and then transferred to molecular oxygen to re-oxidize FAD. CBDA and THCA are synthesized from the ionic intermediates via stereoselective cyclization by the enzymes. As also noted in FIG. 3, the hydride ion is transferred from the reduced flavin to molecular oxygen, resulting in the formation of hydrogen peroxide ($H_2O_2$) and re-activation of the flavin for the next cycle. As a result, in addition to producing CBDA and THCA respectively, this reaction produces hydrogen peroxide which is naturally toxic to the host cell. Due to this production of a toxic hydrogen peroxide byproduct, cannabinoid synthesis generates a self-limiting feed-back loop preventing high-level production and/or accumulation of cannabinoids in in vivo systems.

*Cannabis* plants deal with these cellular cytotoxic effects is through a process of directing cannabinoid production to extracellular structures. Specifically, cannabinoid biosynthesis is localized in the secretory cavity of the glandular trichomes which are abundant on the surface of the female inflorescence in *Cannabis sativa*. Trichomes can be visualized as small hairs or other outgrowths from the epidermis of a *Cannabis* plant. For example, Tetrahydrocannabinolic acid (THCA) synthase is a water-soluble enzyme that is responsible for the production of THC. For example, as generally shown in FIG. 4, THC biosynthesis occurs in glandular trichomes and begins with condensation of geranyl pyrophosphate with olivetolic acid to produce cannabigerolic acid (CBGA); the reaction is catalyzed by an enzyme called geranylpyrophosphate:olivatolate geranyl-transferase. CBGA then undergoes oxidative cyclization to generate tetrahydrocannabinolic acid (THCA) in the presence of THCA synthase. THCA is then transformed into THC by non-enzymatic decarboxylation. Sub-cellular localization studies using RT-PCR and enzymatic activity analyses demonstrate that THCA synthase is expressed in the secretory cells of glandular trichomes, and then is translocated into the secretory cavity where the end product THCA accumulates. THCA synthase present in the secretory cavity is functional, indicating that the storage cavity is the site for THCA biosynthesis and storage. In this way, the *Cannabis* is able to produce cannabinoids extracellularly and thereby avoid the cytotoxic effects of these compounds. In addition to cannabinoids, trichomes in *Cannabis* are also the sites of production of other secondary compounds like terpenes, which are responsible for the distinctive aroma of *Cannabis*. As such, the ability of *Cannabis* plants to produce and accumulate cannabinoids and terpenes is limited by the number and size of the plant's trichomes. As a result, the ability of *Cannabis* plant to produce and accumulate cannabinoids and terpenes is limited by the number of trichomes that are present. Increasing trichome density will increase production of cannabinoids and terpenes in *Cannabis*.

Efforts to generate *Cannabis* strains that produce or accumulate high levels of cannabinoids have raised a number of technical problems. Chief among them is the fact that cannabinoid synthesis produces toxic by-products. Notably, both CBDA and THCA synthases require molecular oxygen, in conjunction with a molecule of FAD, to oxidize Cannabigerolic acid (CBGA). Specifically, as shown in FIG. 3, two electrons from the substrate are accepted by an enzyme-bound FAD, and then transferred to molecular oxygen to re-oxidize FAD. CBDA and THCA are synthesized from the ionic intermediates via stereoselective cyclization by the enzymes. The hydride ion is transferred from the reduced flavin to molecular oxygen, resulting in the formation of hydrogen peroxide and re-activation of the flavin for the next cycle. As a result, in addition to producing CBDA and THCA respectively, this reaction produces hydrogen peroxide ($H_2O_2$) which is naturally toxic to the host cell. Due to this production of a toxic hydrogen peroxide byproduct, cannabinoid synthesis generates a self-limiting feed-back loop preventing high-level production and/or accumulation of cannabinoids in in vivo systems. One way that *Cannabis* plants deal with these cellular cytotoxic effects is through the use of trichomes for Cannabinoid production and accumulations.

As will be discussed in more detail below, the current inventive technology overcomes the limitations of cannabinoid production systems while meeting the objectives of a truly effective high-level cannabinoid production and accumulation system.

SUMMARY OF THE INVENTION(S)

The current inventive technology includes systems and methods for enhanced or increased production and/or accumulation of cannabinoids. In one embodiment, the invention may include systems and methods for enhanced production and/or accumulation of cannabinoids in an in planta system. The inventive technology may allow for certain transgenes to be introduced to these plant strains that result in the over-production and/or accumulation of cannabinoids above wild-type levels. In one preferred embodiment, such transgenic plants may exhibit enhanced or increased formation and density of trichome structures which may increase the plant's biosynthesis capacity of cannabinoids, such as THCs, CBCs and CBDs as well as cannabinoid precursor compounds, such as THCA (tetrahydrocannabinolic acid), CBCA (cannabichromenic acid), and CBDA (cannabidiolic acid).

One aim of the current inventive technology may be to generate a genetically modified or transgenic *Cannabis* plant that overexpresses one or more transcription factors that enhance metabolite flux through the cannabinoid biosynthetic pathway. In one preferred embodiment, these transcription factors and their analogues may include certain endogenous and/or heterologous transcription factors. In certain preferred embodiment, one or more of these myb transcription factors may be operably linked to one or more promoters forming an expression vector that may be used to transform a target plant.

Another aim of the current inventive technology may be to generate a genetically modified or transgenic *Cannabis* plant that overexpresses one or more myb transcription factors that enhance metabolite flux through the cannabinoid biosynthetic pathway. In one preferred embodiment, these transcription factors and their analogues. In certain preferred embodiment, one or more of these transgenes may be operably linked to one or more promoters forming an expression vector that may be used to transform a target plant.

Another aim of the current inventive technology may be to generate a genetically modified or transgenic *Cannabis* plant that expresses one or more exogenous/heterologous transcription factors or an analogue that up-regulates trichome formation which may increase the plant's capacity to produce and accumulate cannabinoid and terpene structures. In certain preferred embodiments, one or more of these exogenous transgenes may be operably linked to one or more promoters forming an expression vector that may be used to stably transform a target *Cannabis* or hemp plant—the terms being generally interchangeable as used herein.

Another aim of the current inventive technology may be to generate a genetically modified or transgenic *Cannabis* plant that expresses or overexpresses a heterologous MYB transcription factor from *Artemisia annua* that may increase trichome density, and trichome initiation and proliferation when overexpressed in *Cannabis*. In certain preferred embodiments, one or more of a heterologous MYB transcription factor from *Artemisia annua* may be operably linked to one or more promoters forming an expression vector that may be used to stably transform a target *Cannabis* plant or hemp plant.

One aim of the current inventive technology may be to generate a genetically modified or transgenic *Cannabis* plant that overexpresses one or more transcription factors that enhance metabolite flux through the cannabinoid biosynthetic pathway. In one preferred embodiment, these transcription factors may include various analogues. In certain preferred embodiment, one or more of these transgenes may be operably linked to one or more promoters. Another aim of the current inventive technology may be to generate a genetically modified or transgenic *Cannabis* plants that overexpresses one or more transcription factors, such as heterologous myb transcriptions factors such as MYB8 from *Humulus lupulus* or MYB12 from *Arabidopsis*, that enhance metabolite flux through the cannabinoid biosynthetic pathway. In one preferred embodiment, these transgenes may be operably linked to one or more promoters.

Another aim of the current inventive technology may be to generate a genetically modified or transgenic *Cannabis* plant that expresses one or more exogenous/heterologous transcription factors that up-regulated trichome formation to increase cannabinoid accumulation. In certain preferred embodiments, one or more of these exogenous transgenes may be operably linked to one or more promoters. Another aim of the current inventive technology may be to generate a genetically modified or transgenic *Cannabis* plant that expresses one or more myb transcription factors from *Artemisia annua* that up-regulate trichome formation to increase cannabinoid accumulation. In certain preferred embodiments, one or more of these exogenous transgenes may be operably linked to one or more promoters.

In one aspect, a myb transcription factor, such as aaMYB can be co-expressed with other MYB transcription factors for enhanced cannabinoid biosynthesis, such as *Humulus lupulus* MYB8 or *Arabidopsis* MYB12. In yet further aspects, co-expression of a MYB transcription factor, such as aaMYB with unmodified CBDA synthase may enhance enhanced trichome formation and enhanced production of CBDA synthase in the trichome.

Another aim of the current inventive technology may include the generation of one or more of the above referenced genetically modified plants utilizing *Agrobacterium* Ti-plasmid mediated transformation.

Additional aspects of the invention may include one or more of the following preferred embodiments:
1. A method of increasing trichome formation in a plant comprising the steps:
   stably transforming a cannabinoid producing plant to express a heterologous polynucleotide sequence according to SEQ ID NO. 7, wherein expression of the heterologous polynucleotide sequence upregulates trichome formation in said cannabinoid producing plant.
2. The method of embodiment 1 wherein said cannabinoid producing plant is *Cannabis sativa* or hemp.

3. The method of embodiment 2 wherein the nucleotide sequence SEQ ID NO. 7 is operably linked to a promoter to produce an expression vector and wherein said expression vector is configured to be introduced via transformation to a Cannabis sativa or hemp plant.

4. The method of embodiment 3 wherein the Cannabis sativa or hemp plant is stably transformed through Agrobacterium Ti-plasmid mediated transformation.

5. A genetically modified Cannabis sativa or hemp plant or part thereof produced by the method of embodiment 4.

6. A genetically modified Cannabis sativa or hemp plant or part thereof produced by the method of embodiment 3.

7. The genetically modified Cannabis sativa or hemp plant or part thereof and its progeny of embodiment 6 wherein the plant produces 30% more trichome structures compared to a wild-type Cannabis sativa or hemp plant.

8. The genetically modified Cannabis sativa or hemp plant or part thereof of embodiment 7 wherein its progeny is a seed from the genetically modified Cannabis sativa or hemp plant.

9. The genetically modified Cannabis sativa or hemp plant or part thereof of embodiment 6 wherein said heterologous polynucleotide sequence according to SEQ ID NO. 7 encodes a heterologous polypeptide according to the amino acid sequence SEQ ID NO. 6 wherein expression of the polynucleotide upregulates trichome formation.

10. The genetically modified Cannabis sativa or hemp plant or part thereof and its progeny of embodiment 9 wherein said nucleotide sequence according to SEQ ID NO. 7 that has been codon optimized for expression in Cannabis sativa or hemp.

11. A method of increasing cannabinoid formation in a plant comprising the steps:
stably transforming a cannabinoid producing plant to express a heterologous polynucleotide sequence according to SEQ ID NO. 7, wherein expression of the heterologous polynucleotide sequence upregulates formation of CBDA and/or THCA in said cannabinoid producing plant, and upregulates trichome formation in said cannabinoid producing plant.

12. The method of embodiment 11 wherein said cannabinoid producing plant is Cannabis sativa or hemp.

13. The method of embodiment 12 wherein the nucleotide sequence SEQ ID NO. 7 is operably linked to a promoter to produce an expression vector and wherein said expression vector is configured to be introduced via transformation to a Cannabis sativa or hemp plant.

14. A genetically modified Cannabis sativa or hemp plant or part thereof produced by the method of embodiment 13.

15. A genetically modified Cannabis sativa or hemp plant or part thereof produced by the method of embodiment 12.

16. The genetically modified Cannabis sativa or hemp plant or part thereof and its progeny of embodiment 15 wherein said plant or parts thereof and its progeny express the amino sequence according to SEQ ID NO. 6 wherein expression of the polynucleotide upregulates formation of CBDA and/or THCA.

17. The genetically modified Cannabis sativa or hemp plant or part thereof and its progeny of embodiment 16 wherein the plant produces 4-fold the amount of THCA compared to a wild-type plant, 3-fold the amount of compared to a wild-type plant, and 30% more trichome structures compared to a wild-type plant.

18. The genetically modified Cannabis sativa or hemp plant or part thereof of embodiment 18 wherein its progeny is a seed from the genetically modified Cannabis sativa or hemp plant.

19. The genetically modified Cannabis sativa or hemp plant or part thereof and its progeny of embodiment 15 wherein said nucleotide sequence according to SEQ ID NO. 7 that has been codon optimized for expression in Cannabis sativa or hemp.

20. A method of increasing trichome formation in a plant comprising the steps:
stably transforming a cannabinoid producing plant to express a heterologous polynucleotide sequence encoding transcription factor MYB1 from Artemisia annua, wherein expression of the heterologous MYB1 upregulates trichome formation in said cannabinoid producing plant.

21. The method of embodiments 20, wherein said heterologous polynucleotide sequence encoding transcription factor MYB1 from Artemisia annua comprises a heterologous polynucleotide according to SEQ ID NO. 7 that has been codon optimized for expression in Cannabis sativa or hemp.

22. The method of embodiment 21 wherein said cannabinoid producing plant is Cannabis sativa or hemp.

23. The method of embodiment 22 wherein the nucleotide sequence SEQ ID NO. 7 is operably linked to a promoter to produce an expression vector and wherein said expression vector is configured to be introduced via transformation to a Cannabis sativa or hemp plant.

25. A genetically modified Cannabis sativa or hemp plant or part thereof produced by the method of embodiment 23.

26. The genetically modified Cannabis sativa or hemp plant or part thereof and its progeny of embodiment 22 wherein the plant produces 30% more trichome structures compared to a wild-type Cannabis sativa or hemp plant.

Additional aims of the inventive technology will become apparent from the specification, figures and claims below.

BRIEF DESCRIPTION OF THE FIGURES

The above and other aspects, features, and advantages of the present disclosure will be better understood from the following detailed descriptions taken in conjunction with the accompanying figures, all of which are given by way of illustration only, and are not limiting the presently disclosed embodiments, in which.

MODE(S) FOR CARRYING OUT THE INVENTION(S)

Figure 1:
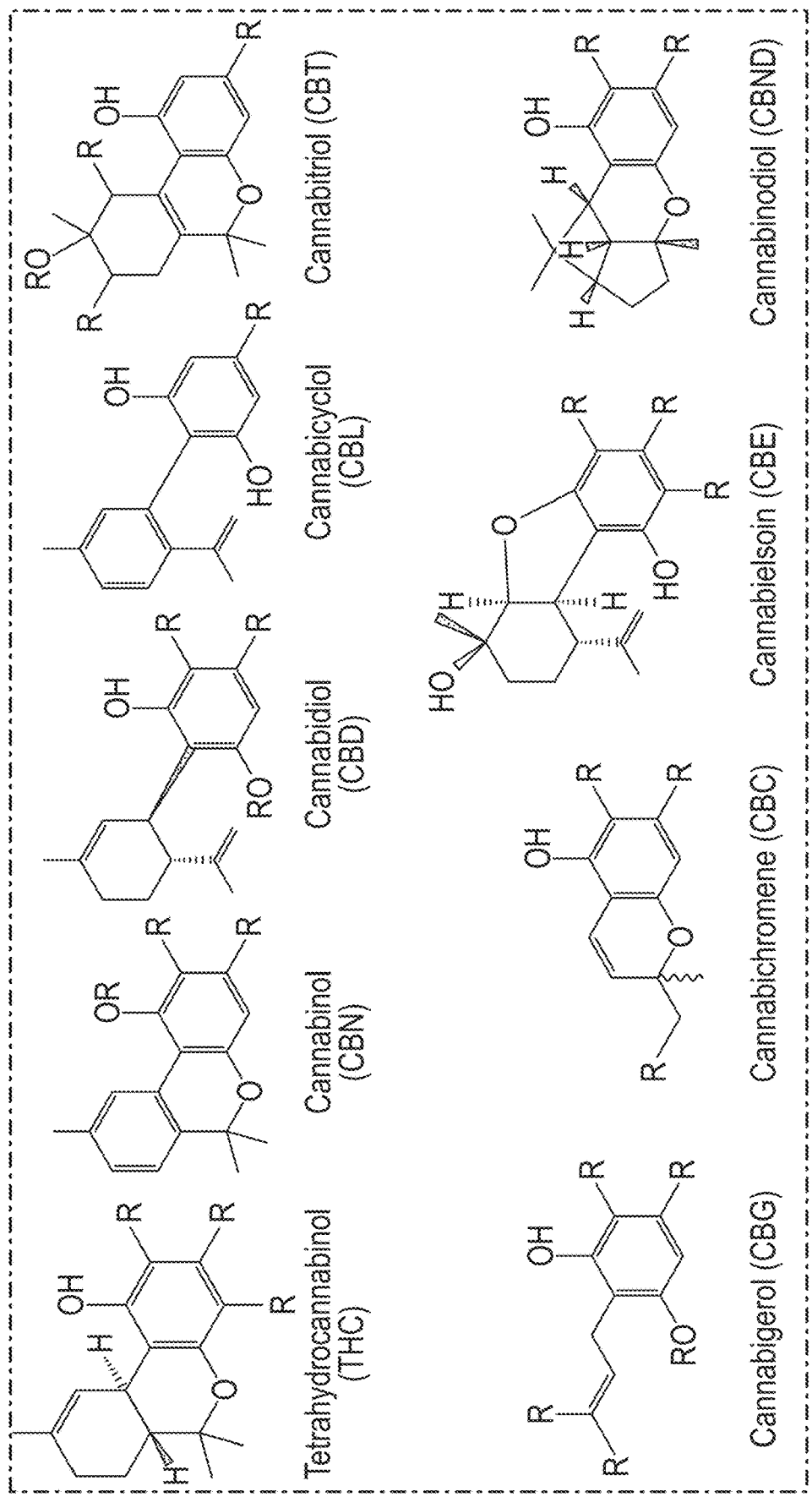
FIG. 1. Synthesis of THC and CBD from common precursor CBGA.
Figure 2:
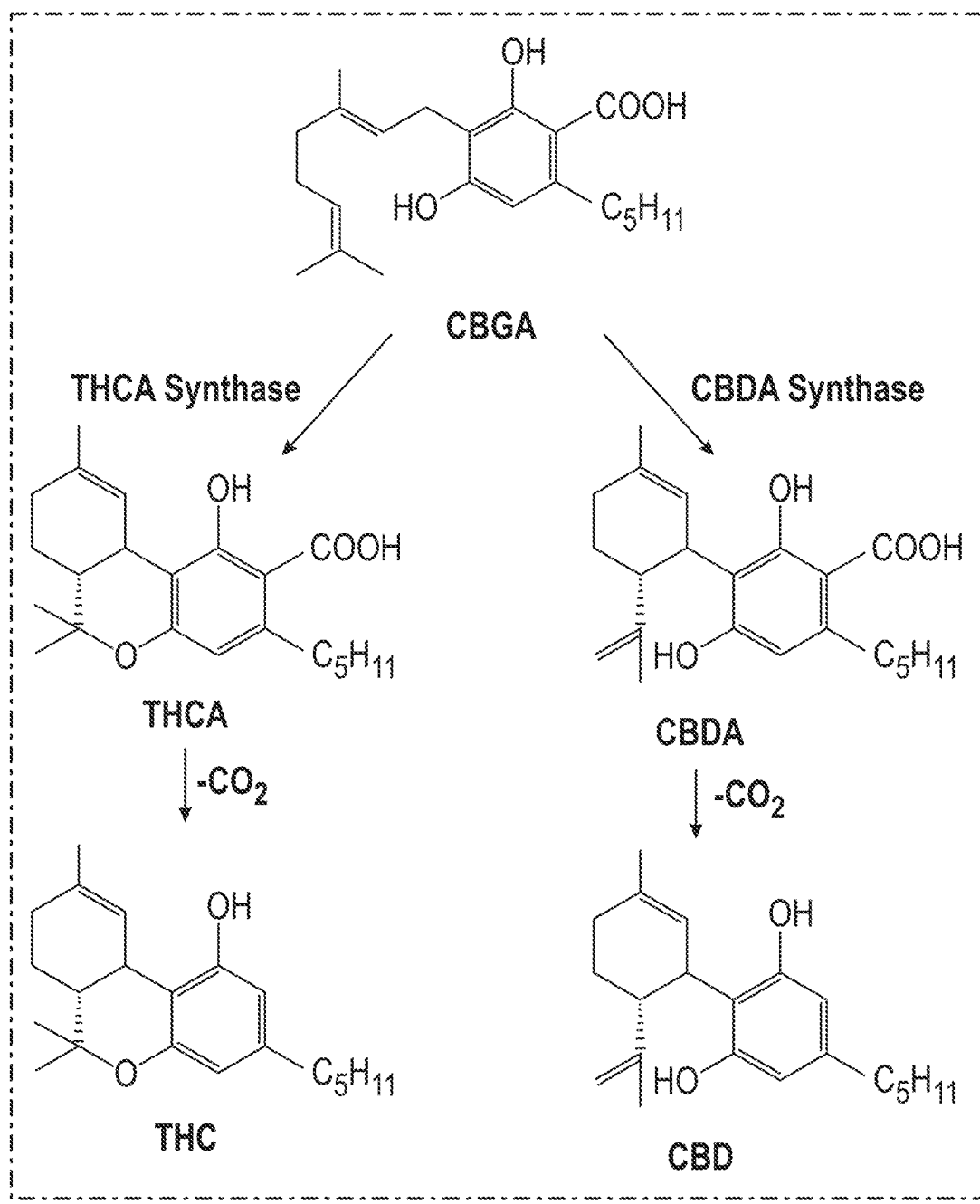
FIG. 2. Synthesis of THC and CBD from common precursor CBGA.
Figure 3:
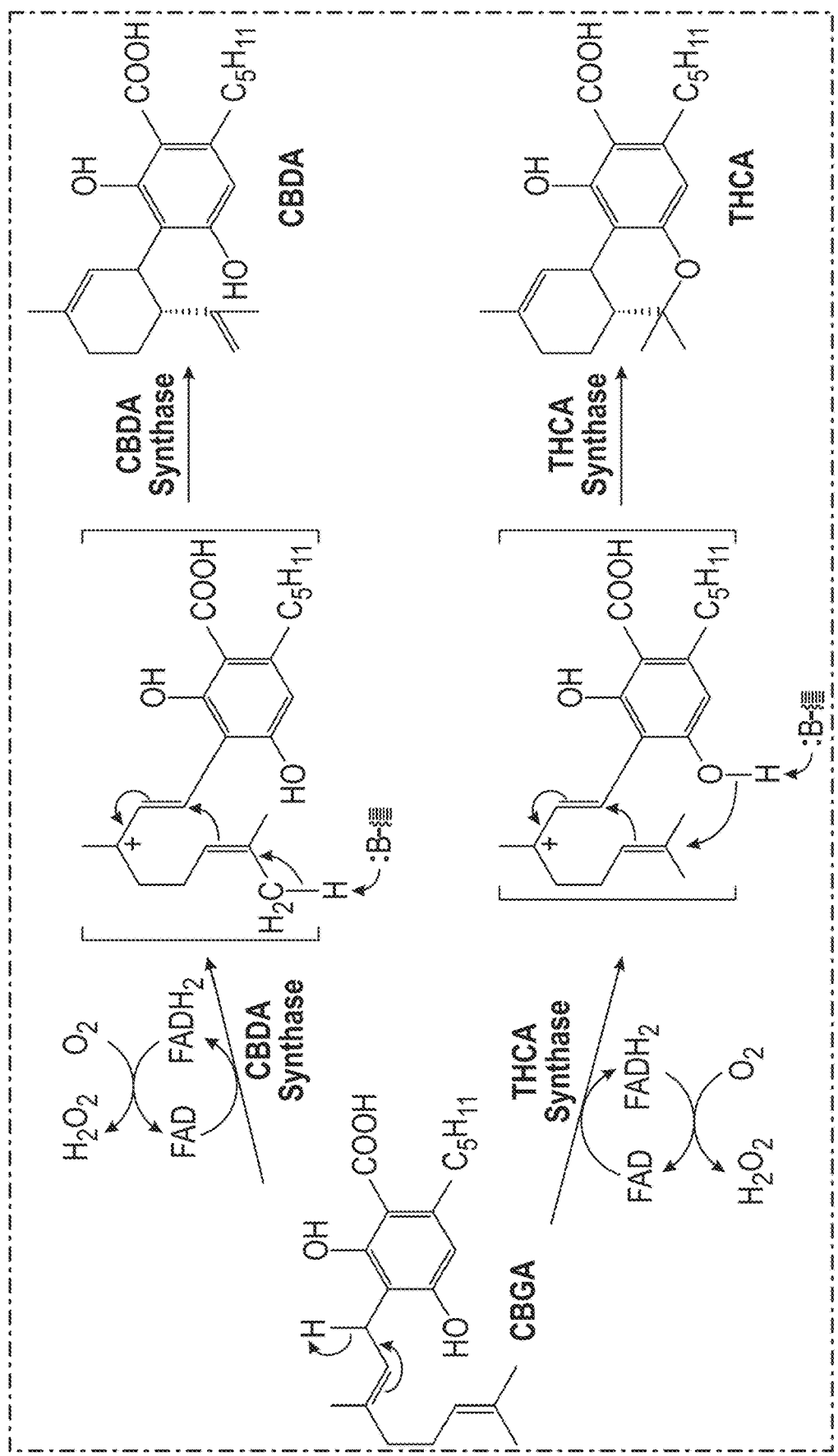
FIG. 3. Schematic diagram of increase cannabinoid production coupled with reduced oxidative damage system in one embodiment thereof.
Figure 4:
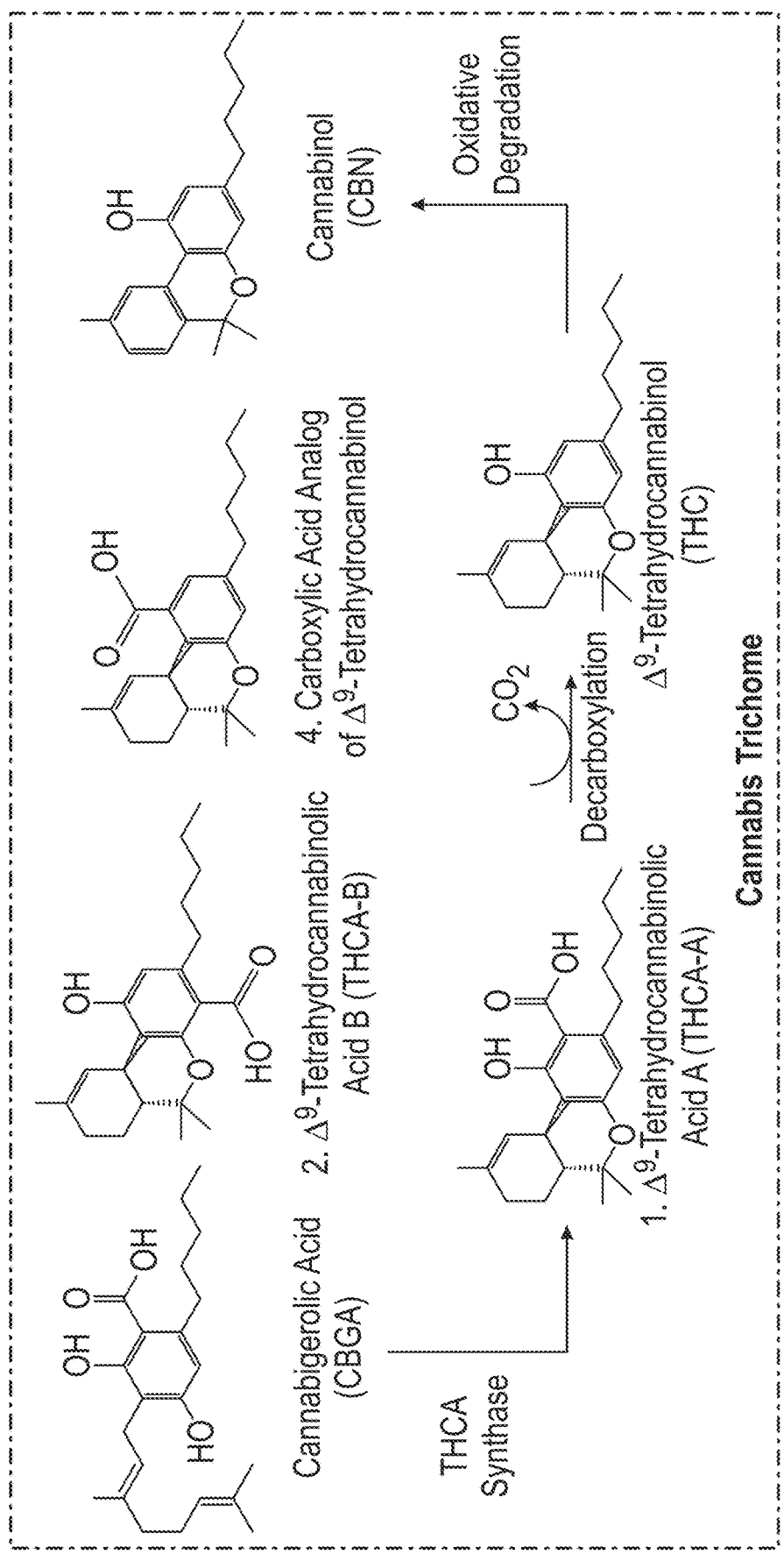
FIG. 4. THCA-A (1) is produced by THCA synthase from its precursor, CBGA, and stored in Cannabis glandular trichomes. THCA-A decarboxylates to form THC, which can further degrade to cannabinol.
Figure 5:
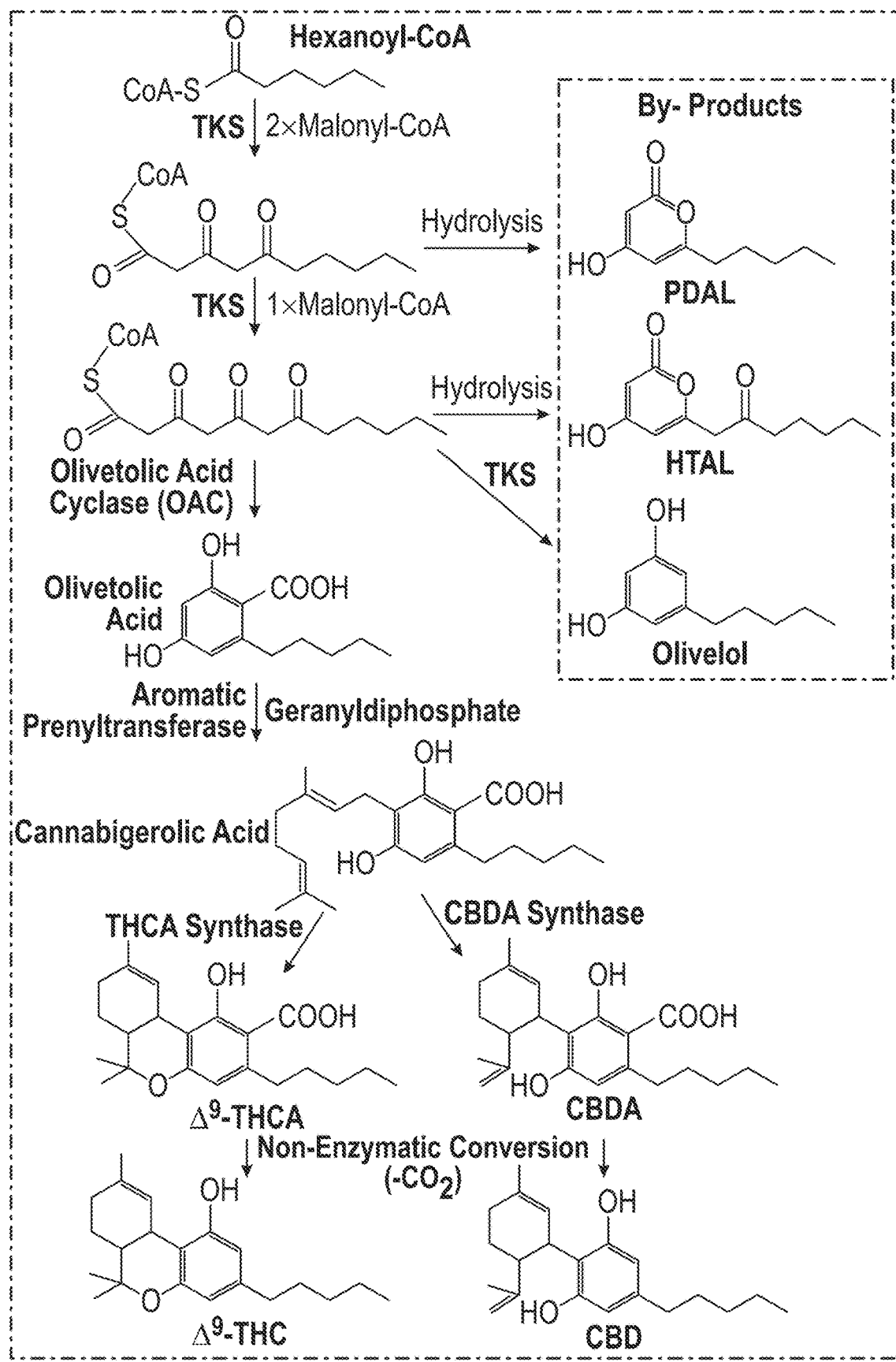
FIG. 5: Synthesis Olivetolic acid a precursor of CBGA.

The inventive technology may include systems and methods for enhanced production and/or accumulation of cannabinoid compounds in an in vivo system. In one preferred embodiment, the invention may include the generation of a genetically modified or transgenic *Cannabis* plant that may produce and/or accumulate one or more cannabinoids at higher than wild-type levels.

In one embodiment, a polynucleotide may be generated that expresses one or more polypeptides related to enhanced trichome formation and density. In certain preferred embodiments, the proteins of the invention may be expressed using any of a number of systems to obtain the desired quantities of the protein. Typically, the polynucleotide that encodes the protein or component thereof is placed under the control of a promoter that is functional in the desired host cell. An extremely wide variety of promoters may be available and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes" or "constructs." Accordingly, the nucleic acids that encode the joined polypeptides are incorporated for high level expression in a desired host cell.

In one preferred embodiment, one or more of the myb transcription factor genes, and/or one or more ortholog genes may be operably linked to a promoter that may be appropriate for protein expression in a *Cannabis* plant. Exemplary promoters may include, but not be limited to: a non-constitutive promoter; an inducible promoter, a tissue-preferred promoter; a tissue-specific promoter, a plant-specific promoter, or a constitutive promoter. In a preferred embodiment, one or more select genes may be operably linked to a leaf-specific gene promoter, such as Cab 1. Additional promoters and operable configurations for expression, as well as co-expression of one or more of the selected genes, are generally known in the art.

Genes encoding a myb transcription factor and/or its ortholog of the invention may be introduced into *Cannabis* plants using several types of transformation approaches developed for the generation of transgenic plants. Standard transformation techniques, such as Ti-plasmid *Agrobacterium*-mediated transformation, particle bombardment, microinjection, and electroporation may be utilized to construct stably transformed transgenic plants and/or cells.

Another embodiment comprises a polynucleotide of a nucleic acid sequence encoding one or more proteins that enhance trichome formation and/or density as herein described. Other embodiments include an expression vector comprising this polynucleotide operably linked to a promoter. A genetically altered plant or parts thereof and its progeny comprising this polynucleotide operably linked to a promoter, wherein said plant or parts thereof and its progeny produce at least one protein that enhances trichome formation and/or density is yet another embodiment, such plant preferably being of the family Cannabaceae. For example, seeds and pollen may contain this polynucleotide sequence or a homologue or ortholog thereof. Moreover, a genetically altered plant cell comprising this polynucleotide operably linked to a promoter such that said plant cell produces one or more cannabinoid production transcription factor proteins. Another embodiment provides for a method for constructing a genetically altered plant or part thereof having increased trichome formation and/or density compared to a non-genetically altered plant or part thereof, the method comprising the steps of: introducing a polynucleotide encoding a protein into a plant or part thereof to provide a genetically altered plant or part thereof, wherein said protein comprising at least one transcription factor protein that increases trichome formation and/or density in said plant, said plant preferably being of the family Cannabaceae, and preferably *Cannabis*.

The inventive technology may include systems and methods for enhanced production and accumulation of cannabinoid compounds in an in vivo system. In one preferred embodiment, the invention may include the generation of a genetically modified or transgenic *Cannabis* plant that may be configured to be capable of forming trichome structures at higher than wild-type levels. Such enhanced trichome may structures may allow for increase capacity by the *Cannabis* plant to produce and accumulate cannabinoids and terpenes. Additional embodiments, as note elsewhere, include the expression of one or more endogenous or heterologous myb transcriptions factors in said *Cannabis* plant to increase metabolic flux through the cannabinoid biosynthesis pathway. In one preferred embodiment, a transient, and/or stable transgenic *Cannabis* plant may be generated to express one or more genes that may up-regulate trichome formation and/or density. In one preferred embodiment, a polynucleotide may be generated that encodes for one or more exogenous or heterologous transcription factors genes, and/or orthologs that up-regulate and/or down-regulated competing pathways, resulting in increased trichome formation. This exogenous polynucleotide may be introduced into *Cannabis*, or other trichome-producing plant that also may synthesize cannabinoids, terpenes or other compounds of interest.

In this preferred embodiment, a polynucleotide may be generated that encodes for one or more exogenous transcription factors genes, specifically aaMYb1 derived from the plant *Artemisia annua*. In this embodiment this codon optimized polynucleotide generated the protein according to (SEQ ID. NO. 5). In another preferred embodiment, a polynucleotide according to SEQ ID NO. 6 may be generated that is codon optimized for expression in *Cannabis* and further encodes for one or more exogenous transcription factors genes, specifically aaMYb1 derived from the plant *Artemisia annua*. In this embodiment this codon optimized polynucleotide generated the protein according to (SEQ ID. NO. 5). Additional embodiments of the invention may include a polynucleotide that encodes for one or more exogenous orthologs of AaMYb1, which may be expressed in a plant, and preferably a *Cannabis* plant and upregulate trichome formation and/or density. In this embodiment, a polynucleotide that encodes for one or more exogenous orthologs of AaMYb1 may include the sequences identified as AtMYB86 (SEQ ID. NO. 10), AtMYB55 (SEQ ID. NO. 11), AtMYB50 (SEQ ID. NO. 12), AtMYB61 (SEQ ID. NO. 13).

Figure 7:
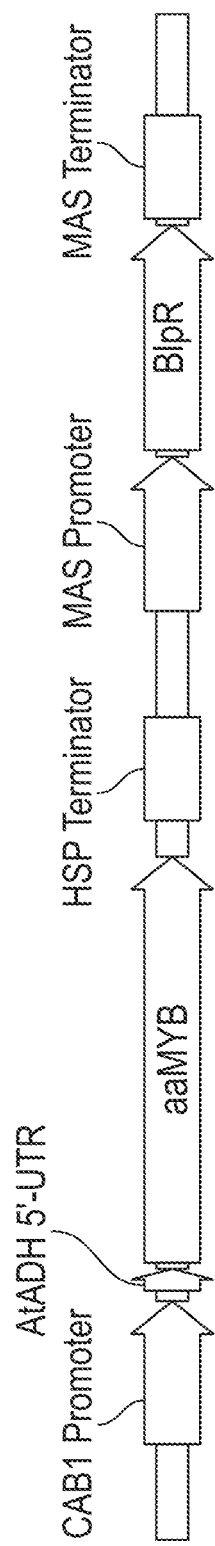
FIG. 7: Expression cassette for enhancing trichome density in Cannabis sativa. aaMYB, Artemisia annua MYB transcription; HSP terminator, efficient transcription terminator from the Arabidopsis thaliana heat shock protein 18.2 gene; CAB1 promoter, Chlorophyll a/b binding protein promoter for expression in leaves; AtADH 5' UTR, Arabidopsis Alcohol dehydrogenase translational enhancer; MAS promoter, MAS terminator, promoter and terminator regions of the mannopine synthetase (mas) gene.

In another preferred embodiment, a polynucleotide according to SEQ ID NO. 7, may be generated that is codon optimized for expression in *Cannabis* and further encodes for one or more exogenous transcription factors genes, specifically aaMYb1 derived from the plant *Artemisia annua*. In this embodiment this codon optimized polynucleotide generated the protein according to (SEQ ID. NO. 6). As shown in FIG. 7, a polynucleotide according to SEQ ID NO. 7 may be part of an expression vector that may be introduced to a plant, and preferably a *Cannabis* plant. Again referring to FIG. 7, in this preferred embodiment, a binary expression vector for overexpressing aaMYB1 (also designated as aaMYB) may be generated designed and constructed in the commercial vector pRI201-AN (Takara Bio USA), a binary vector for high-level expression of a foreign gene in dicotyledonous plants carrying the constitutive 35S promoter and an *Arabidopsis* Alcohol dehydrogenase (AtAdh) as a translational enhancer. This binary expression vector may be used to transform a trichome producing plant, such as *Cannabis* where it may be overexpressed and produce a protein according to amino acid sequence SEQ ID NO. 6. This expression vector for overexpressing aaMYB1 may further be used to generate stable *Cannabis* plant transformation.

Additional embodiments of the invention may include a polynucleotide that encodes for one or more exogenous orthologs of AaMYb1, which may be expressed in a plant, and preferably a *Cannabis* plant and upregulate trichome formation and/or density. In this embodiment, a polynucleotide that encodes for one or more exogenous orthologs of AaMYb1 may include the sequences identified as AtMYB86 (SEQ ID. NO. 10), AtMYB55 (SEQ ID. NO. 11), AtMYB50 (SEQ ID. NO. 12), AtMYB61 (SEQ ID. NO. 13).

Again, a polynucleotide that encodes for one or more exogenous orthologs of AaMYb1 may include the sequences identified as amino acid sequence AtMYB86 (SEQ ID. NO. 10), AtMYB55 (SEQ ID. NO. 11), AtMYB50 (SEQ ID. NO. 12), or AtMYB61 (SEQ ID. NO. 13). One or more of said polynucleotide that encodes for one or more exogenous orthologs of AaMYb1 may be part of an expression vector that may be introduced to a plant, and preferably a *Cannabis* plant. Again referring to FIG. 7, in this preferred embodiment, a binary expression vector for overexpressing one or more exogenous orthologs of AaMYb1 may be generated designed and constructed in the commercial vector pRI201-AN (Takara Bio USA), a binary vector for high-level expression of a foreign gene in dicotyledonous plants carrying the constitutive 35S promoter and an *Arabidopsis* Alcohol dehydrogenase (AtAdh) as a translational enhancer. This binary expression vector may be used to transform a trichome producing plant, such as *Cannabis* where it may be overexpressed and produce a protein according to amino acid sequence AtMYB86 (SEQ ID. NO. 10), AtMYB55 (SEQ ID. NO. 11), AtMYB50 (SEQ ID. NO. 12), or AtMYB61 (SEQ ID. NO. 13). one or more of the expression vectors described above may be used for overexpressing aaMYB1 or one of its orthologs in a plant, and preferably *Cannabis*, and may further be used to generate stable *Cannabis* plant transformation.

In one embodiment, a polynucleotide may be generated that expresses one or more heterologous MYB transcription factors related to enhanced trichome formation and density as identified in SEQ ID NO 6, or a homolog or ortholog thereof. In one embodiment, a polynucleotide may be generated that expresses a heterologous aaMYB transcription factor protein (SEQ ID NO. 6). In certain preferred embodiments, the aaMYB transcription factor of the invention may be expressed using any of a number of systems to obtain the desired quantities of the protein. Typically, the polynucleotide that encodes the aaMYB or component thereof is placed under the control of a promoter that is functional in the desired host cell. An extremely wide variety of promoters may be available and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes" or "constructs." Accordingly, the nucleic acids that encode the joined polypeptides are incorporated for high level expression in a desired host cell.

In one preferred embodiment, a heterologous aaMYB polynucleotide according to the sequence identified as SEQ ID NO. 7, and/or one or more ortholog genes may be operably linked to a promoter that may be appropriate for protein expression in a *Cannabis* plant. Exemplary promoters may include, but not be limited to: a non-constitutive promoter; an inducible promoter, a tissue-preferred promoter; a tissue-specific promoter, a plant-specific promoter, or a constitutive promoter. In a preferred embodiment, one or more select genes may be operably linked to a leaf-specific gene promoter, such as Cab 1. Additional promoters and operable configurations for expression, as well as co-expression of one or more of the selected genes, are generally known in the art.

Genes encoding a heterologous aaMYB polynucleotide according to the sequence identified as SEQ ID NO. 7, and/or one or more ortholog genes of the invention may be introduced into *Cannabis* plants using several types of transformation approaches developed for the generation of transgenic plants. Standard transformation techniques, such as Ti-plasmid *Agrobacterium*-mediated transformation, particle bombardment, microinjection, and electroporation may be utilized to construct stably transformed transgenic plants and/or cell.

Another embodiment comprises a polynucleotide of a nucleic acid sequence encoding a heterologous aaMYB polynucleotide according to the sequence identified as SEQ ID NO. 6, that enhance trichome formation and/or density as herein described. Other embodiments include an expression vector comprising a heterologous aaMYB polynucleotide according to the sequence identified as SEQ ID NO. 7 operably linked to a promoter. A genetically altered plant or parts thereof and its progeny express a heterologous aaMYB polynucleotide according to the sequence identified as SEQ ID NO. 6 operably linked to a promoter, wherein said plant or parts thereof and its progeny have enhanced trichome formation and/or density is yet another embodiment; such plant preferably being of the family Cannabaceae. In this embodiment, seeds and pollen may contain this polynucleotide sequence or a homologue or ortholog thereof of a heterologous aaMYB polynucleotide according to the sequence identified as SEQ ID NO. 7. Moreover, a genetically altered *Cannabis* plant comprising a heterologous aaMYB polynucleotide according to the sequence identified as SEQ ID NO. 7 operably linked to a promoter such that said *Cannabis* plant expresses a protein according to SEQ ID NO. 6 and has enhanced trichome formation and/or density.

Another embodiment provides for a method for constructing a genetically altered plant or part thereof having increased trichome formation and/or density compared to a non-genetically altered plant or part thereof, the method comprising the steps of: introducing a polynucleotide encoding a heterologous aaMYB polynucleotide according to the sequence identified as SEQ ID NO. 7, into a plant or part thereof to provide a genetically altered plant or part thereof, wherein said heterologous aaMYB polynucleotide according to the sequence identified as SEQ ID NO. 7, encodes at least one transcription factor protein that increases trichome formation and/or density in said plant, said plant preferably being of the family Cannabaceae, and more preferably *Cannabis*.

The inventive technology may include systems and methods for enhanced production and accumulation of cannabinoid compounds in an in vivo system. In one preferred embodiment, the invention may include the generation of a genetically modified or transgenic *Cannabis* plant that may be configured to be capable of forming trichome structures at higher than wild-type levels through expression of heterologous aaMYB polynucleotide according to the sequence identified as SEQ ID NO. 7. Such enhanced trichome may structures may allow for increase capacity by the *Cannabis* plant to produce and accumulate cannabinoids and terpenes. Additional embodiments, as noted elsewhere, include the expression of one or more endogenous or heterologous myb transcriptions factors in said *Cannabis* plant to increase metabolic flux through the cannabinoid biosynthesis pathway.

Additional embodiments of the invention may include one or more polynucleotides that encode one or more homologous aaMYB1 transcription factor genes according to the sequence identified as SEQ ID NO. 6 or 7, and/or one or more homologous orthologs as identified herein. For example, in some embodiments, a homologous sequences may have from about 70-100%, or more generally 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 99.9%.

In one embodiment, a polynucleotide may be generated that expresses one or more of the of the sequences identified in SEQ ID NOs 7, wherein such polynucleotide encodes a MYB transcription factor that enhances trichome formation and/or density as identified herein. In certain preferred embodiments, the proteins, according the sequences identified in SEQ ID NOs 6 of the invention, may be expressed using any of a number of systems to obtain the desired quantities of the protein. Typically, the polynucleotide that encodes the protein or component thereof is placed under the control of a promoter that is functional in the desired host cell. An extremely wide variety of promoters may be available and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes" or "constructs." Accordingly, the nucleic acids that encode the joined polypeptides are incorporated for high level expression in a desired host cell.

In one preferred embodiment, a Myb transcription factor gene having a sequence identified in SEQ ID NOs 7, and/or one or more of its exogenous ortholog genes, may be operable linked to a promoter that may be appropriate for protein expression in a *Cannabis* plant.

Exemplary promoters may include, but not be limited to: a non-constitutive promoter; an inducible promoter, a tissue-preferred promoter; a tissue-specific promoter, a plant-specific promoter, or a constitutive promoter. In a preferred embodiment, one or more select genes may be operably linked to a leaf-specific gene promoter, such as Cab 1. Additional promoters and operable configurations for expression, as well as co-expression of one or more of the selected genes are generally known in the art.

Genes encoding a Myb transcription factor gene having a sequence identified in SEQ ID NOs 7 that generate enhanced trichome formation and density transcriptions factors and/or their orthologs of the invention may be introduced into *Cannabis* plants using several types of transformation approaches developed for the generation of transgenic plants. Standard transformation techniques, such as Ti-plasmid *Agrobacterium*-mediated transformation, particle bombardment, microinjection, and electroporation may be utilized to construct stably transformed transgenic plants.

Another embodiment comprises a polynucleotide sequence encoding one or more Myb transcription factor genes having a sequence identified in SEQ ID NOs 7. Another embodiment includes an expression vector comprising this polynucleotide having a sequence identified in SEQ ID NOs 7 operably linked to a promoter. A genetically altered plant or parts thereof and its progeny comprising a polynucleotide having a sequence identified in SEQ ID NOs 7 operably linked to a promoter, wherein said plant or parts thereof and its progeny express a polynucleotide sequence identified in SEQ ID NOs 7 is yet another embodiment, such plant preferably being of the family Cannabaceae, and more preferably *Cannabis* or hemp. For example, seeds and pollen contain one or more of said polynucleotide sequences or a homologues thereof, a genetically altered plant cell comprising one or more of said polynucleotides operably linked to a promoter such that said plant cell produces one or more transcription factor proteins according to sequence identified as SEQ ID NOs 6, and where said plant have enhance trichome formation and/or density. Another embodiment comprises a tissue culture comprising a plurality of the genetically altered plant cells.

Another embodiment provides a method for constructing a genetically altered plant or part thereof having increased trichome formation compared to a non-genetically altered plant or part thereof, the method comprising the steps of: introducing a polynucleotide according to SEQ ID NOs 7 into a plant or part thereof to provide a genetically altered plant or part thereof, wherein said polynucleotide encode a protein comprising at least one trichome accumulation transcription factor protein according to SEQ ID NOs 6.

Additional embodiments may include selecting a genetically altered plant or part thereof that expresses the trichome accumulation transcription factor protein, wherein the expressed protein has trichrome formation capabilities. In certain embodiments, a polynucleotide encoding the trichome accumulation transcription factor protein is introduced via transforming said plant with an expression vector comprising said polynucleotide operably linked to a promoter. The trichome accumulation transcription factor protein may comprise a SEQ ID selected from the group consisting of according to SEQ ID NOs 7, 10, 11, 12, or 13 or homologues thereof. In one embodiment, the invention may encompass a system to increase overall cannabinoid production and accumulation in trichomes. The invention may include, in a preferred embodiment, creating a transgenic *Cannabis* plant that overexpresses transcription factor AtMyb12 and/or AaMYB1 to increase overall cannabinoid biosynthesis and accumulation in trichomes, respectively.

Another embodiment comprises a combination polynucleotide of a nucleic acid sequence encoding a combination of: 1) a trichome accumulation transcription factor protein; 2) a cannabinoid production transcription factor protein; 3) and/or 3) a chimera protein, or any homologue thereof. A genetically altered plant or parts thereof and its progeny comprising this combination polynucleotide operably linked to a promoter, wherein said plant or parts thereof and its progeny produce said protein is yet another embodiment. For example, seeds and pollen contain this polynucleotide sequence or a homologue thereof, a genetically altered plant comprising this polynucleotide operably linked to a promoter such that said plant cell produces said proteins.

Additional embodiments may include selecting a genetically altered plant or part thereof that expresses one or more of the proteins, wherein the expressed protein(s) may have: 1) increased cannabinoid production capabilities; 2) increased trichome formation capabilities. In certain embodiments, a combination polynucleotide encoding the proteins is introduced via transforming said plant with an expression vector comprising said combination polynucleotide operably linked to a promoter. The cannabinoid production transcription factor protein may comprise a SEQ ID selected from the group consisting of SEQ ID NO: 1, 2, 3, 4, 5, or homologues thereof. The trichome accumulation transcription factor protein may comprise a SEQ ID selected from the group consisting of SEQ ID NO: 6, 10, 11, 12, or 13 or homologues thereof.

In one preferred embodiment, a combination polynucleotide encoding one or more of the above identified proteins may be operable linked to a promoter that may be appropriate for protein expression in a *Cannabis* plant. Exemplary promoters may include, but not be limited to: a non-constitutive promoter; an inducible promoter, a tissue-preferred promoter; a tissue-specific promoter, a plant-specific promoter, or a constitutive promoter. In a preferred embodiment, one or more select genes may be operably linked to a leaf-specific gene promoter, such as Cab 1. Additional promoters and operable configurations for expression, as well as co-expression of one or more of the selected genes are generally known in the art.

Genes encoding by a combination polynucleotide and/or a homologue thereof, may be introduced into *Cannabis* plants using several types of transformation approaches developed for the generation of transgenic plants. Standard transformation techniques, such as Ti-plasmid *Agrobacterium*-mediated transformation, particle bombardment, microinjection, and electroporation may be utilized to construct stably transformed transgenic plants. In one embodiment, a transgenic *Cannabis* plant may be generated to express one or more *Cannabis sativa* transcription factors that may enhance the cannabinoid metabolic pathway(s). In one preferred embodiment, a polynucleotide may be generated that encodes for one or more *Cannabis sativa* myb transcription factors genes, and/or one or more exogenous ortholog genes that enhance the metabolite flux through the cannabinoid biosynthetic pathway.

Figure 6:
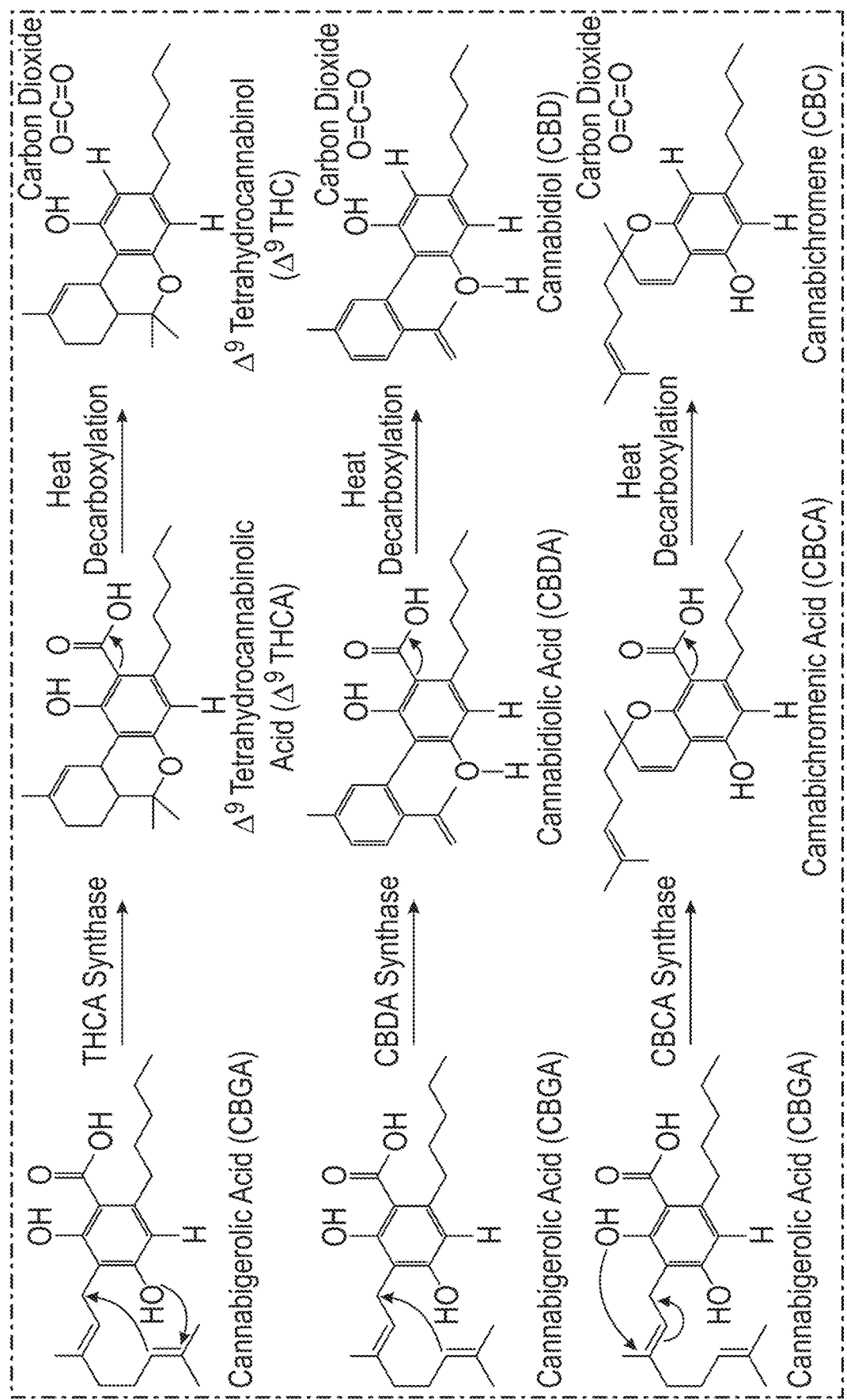
FIG. 6: Synthesis of THC, CBD and CBC from CBGA precursor.

In this preferred embodiment, a polynucleotide may be generated that encodes for one or more *Cannabis sativa* myb transcription factors genes, specifically CAN833 and/or CAN738 that, as shown in, may drive the production of Olivetolic acid, which is a precursor of CBGA, which in turn is a precursor in the biosynthetic pathway of THCs, CBDs and CBC shown below in FIG. 6. In an alternative embodiment also highlighted below, a polynucleotide may be generated that encodes for one or more *Cannabis sativa* myb transcription factors genes orthologs, specifically Myb8, AtMyb12, and/or MYB112 that may also drive the production of Olivetolic acid, which is a precursor of CBGA, which in turn is a precursor in the biosynthetic pathway of THCs, CBDs and CBC.

Additional embodiments of the invention may include one or more polynucleotides that encode one or more homologous *Cannabis sativa* myb transcription factors genes, and or orthologs. For example, in some embodiments, a homologous sequence may have from about 70-100%, or more generally 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%.

The inventive technology includes systems and methods for high-level production of cannabinoid compounds. As used herein, the term "high level" in this instance may mean higher than wild-type biosynthesis or accumulation of one or more cannabinoids in a plant or plant cell.

The inventive technology includes systems and methods for production of a *Cannabis* plant having enhanced trichome formation and/or density. As used herein, the term "enhanced" in this instance may mean higher than wild-type amounts, density or size of trichome structures present on a *Cannabis* plant.

Another embodiment of the inventive technology may include systems and methods for enhanced production and/or accumulation of cannabinoid compounds in an in vivo system. In one preferred embodiment, the invention may include the generation of a genetically modified or transgenic *Cannabis* plant that may produce and/or accumulate one or more cannabinoids at higher than wild-type levels. In one embodiment, a transgenic *Cannabis* plant may be generated to express one or more *Cannabis sativa* transcription factors that may enhance the cannabinoid metabolic pathway(s). In one preferred embodiment, a polynucleotide may be generated that encodes for one or more *Cannabis sativa* myb transcription factors genes, and/or one or more exogenous ortholog genes that enhance the metabolite flux through the cannabinoid biosynthetic pathway.

In this preferred embodiment, a polynucleotide may be generated that encodes for one or more *Cannabis sativa* myb transcription factors genes, such as CAN833 and/or CAN738 that. These transcriptions factors may drive the production of olivetolic acid, which is a precursor of CBGA, which in turn is a precursor in the biosynthetic pathway of THCs, CBDs and CBC. In an alternative embodiment, a polynucleotide may be generated that encodes for one or more *Cannabis sativa* myb transcription factors genes orthologs, specifically *cannabis* Myb12 (SEQ IDs. 1-2), Myb8 (SEQ ID NO. 3), AtMyb12 (SEQ ID NO. 44), and/or MYB112 (SEQ ID NO. 5) that may also drive the production of olivetolic acid, which is a precursor of CBGA, which in turn is a precursor in the biosynthetic pathway of THCs, CBDs and CBC.

In another preferred embodiment, a plant Cannabis plant, may be genetically modified to express one or more first myb transcription factors genes that may increase cannabinoid production by increasing metabolic flux through the cannabinoid biosynthesis pathway and further express one or second more myb transcription factors genes that upregulate trichome formation and density. In this preferred embodiment, first myb transcription factors genes that may increase cannabinoid production by increasing metabolic flux through the cannabinoid biosynthesis pathway may be selected from one or more of: a nucleotide sequence that expresses the amino acid sequence identified as SEQ ID NO. 8, a nucleotide sequence that expresses the amino acid sequence identified as SEQ ID NO. 9, the nucleotide sequence identified as SEQ ID NO. 1, a nucleotide sequence that expresses the amino acid sequence identified as SEQ ID NO. 2, amino acid sequence identified as SEQ ID NO. 3, amino acid sequence identified as SEQ ID NO. 4, amino acid sequence identified as SEQ ID NO. 5. A second myb transcription factor that upregulates trichome formation and density may be selected from the one or more of: the amino acid sequence identified SEQ ID. NO. 6, the nucleotide sequence identified as SEQ ID. NO. 7, amino acid sequence identified as SEQ ID. NO. 10, amino acid sequence identified as SEQ ID. NO. 11, amino acid sequence identified as SEQ ID. NO. 12, and/or amino acid sequence identified as SEQ ID. NO. 13.

In another preferred embodiment, a plant Cannabis plant, may be genetically modified to express one or more first myb transcription factors genes that may increase cannabinoid production by increasing metabolic flux through the cannabinoid biosynthesis pathway and further express one or second more myb transcription factors genes that upregulate trichome formation and density.

In this preferred embodiment, a polynucleotide may be generated that encodes for one or more exogenous transcription factors genes, specifically aaMYb1 derived from the plant Artemisia annua. In this embodiment this codon optimized polynucleotide generated the protein according to (SEQ ID. NO. 6). In another preferred embodiment, a polynucleotide according to SEQ ID NO. 7, may be generated that is codon optimized for expression in Cannabis and further encodes for one or more exogenous transcription factors genes, specifically aaMYb1 derived from the plant Artemisia annua. In this embodiment this codon optimized polynucleotide generated the protein according to (SEQ ID. NO. 7). Additional embodiments of the invention may include a polynucleotide that encodes for one or more exogenous orthologs of AaMYb1, which may be expressed in a plant, and preferably a Cannabis plant and upregulate trichome formation and/or density. In this embodiment, a polynucleotide that encodes for one or more exogenous orthologs of AaMYb1 may include the sequences identified as AtMYB86 (SEQ ID. NO. 10), AtMYB55 (SEQ ID. NO. 11), AtMYB50 (SEQ ID. NO. 12), AtMYB61 (SEQ ID. NO. 13). In another embodiment, a plant may be engineered to express, or overexpress one more cannabinoid synthases, for example: CBDA synthase, CBG synthase, CBCA synthase, and THCA synthase.

In one preferred embodiment, the invention may include methods of generating a polynucleotide that expresses one or more of the SEQ IDs related to enhanced cannabinoid production identified herein. In certain preferred embodiments, the proteins of the invention may be expressed using any of a number of systems to obtain the desired quantities of the protein. Typically, the polynucleotide that encodes the protein or component thereof is placed under the control of a promoter that is functional in the desired host cell. An extremely wide variety of promoters may be available and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes" or "constructs." Accordingly, the nucleic acids that encode the joined polypeptides are incorporated for high level expression in a desired host cell.

Additional embodiments of the invention may include selecting a genetically altered plant or part thereof that expresses the cannabinoid production transcription factor protein, wherein the expressed protein has increased cannabinoid biosynthesis capabilities. In certain embodiments, a polynucleotide encoding the cannabinoid production transcription factor protein is introduced via transforming said plant with an expression vector comprising said polynucleotide operably linked to a promoter. The cannabinoid production transcription factor protein may comprise a nucleotide sequence that is codon optimized to be expressed in Cannabis selected from the group consisting of SEQ ID NO: 8-9, or a homologue thereof. Such codon optimized cannabinoid production transcription factor may be co-expressed in Cannabis with a trichome formation transcription factor that has also been optimized for expression in Cannabis according to sequence 7.

It should be noted that a number of combinations and permutations of the genes/proteins described herein may be co-expressed and thereby accomplish one or more of the goals of the current invention. Such combinations are exemplary of preferred embodiments only, and not limiting in any way.

As used herein, a "cannabinoid" is a chemical compound (such as cannabinol, THC or cannabidiol) that is found in the plant species Cannabis among others like Echinacea; Acmella Oleracea; Helichrysum Umbraculigerum; Radula Marginata (Liverwort) and Theobroma Cacao, and metabolites and synthetic analogues thereof that may or may not have psychoactive properties. Cannabinoids therefore include (without limitation) compounds (such as THC) that have high affinity for the cannabinoid receptor (for example Ki<250 nM), and compounds that do not have significant affinity for the cannabinoid receptor (such as cannabidiol, CBD). Cannabinoids also include compounds that have a characteristic dibenzopyran ring structure (of the type seen in THC) and cannabinoids which do not possess a pyran ring (such as cannabidiol). Hence a partial list of cannabinoids includes THC, CBD, dimethyl heptylpentyl cannabidiol (DMHP-CBD), 6,12-dihydro-6-hydroxy-cannabidiol (described in U.S. Pat. No. 5,227,537, incorporated by reference); (3 S,4R)-7-hydroxy-$\Delta$6-tetrahydrocannabinol homologs and derivatives described in U.S. Pat. No. 4,876,276, incorporated by reference; (+)-4-[4-DMH-2,6-diacetoxy-phenyl]-2-carboxy-6,6-dimethylbicyclo[3.1.1]hept-2-en, and other 4-phenylpinene derivatives disclosed in U.S. Pat. No. 5,434,295, which is incorporated by reference; and cannabidiol (−)(CBD) analogs such as (−)CBD-monomethylether, (−)CBD dimethyl ether; (−)CBD diacetate; (−)3'-acetyl-CBD monoacetate; and ±AF11, all of which are disclosed in Consroe et al., J. Clin. Pharmacol. 21:428S-436S, 1981, which is also incorporated by reference. Many other cannabinoids are similarly disclosed in Agurell et al., Pharmacol. Rev. 38:31-43, 1986, which is also incorporated by reference.

As claimed herein, the term "cannabinoid" may also include different modified forms of a cannabinoid such as a hydroxylated cannabinoid or cannabinoid carboxylic acid. For example, if a glycosyltransferase were to be capable of glycosylating a cannabinoid, it would include the term cannabinoid as defined elsewhere, as well as the aforementioned modified forms. It may further include multiple glycosylation moieties.

Examples of cannabinoids are tetrahydrocannabinol, cannabidiol, cannabigerol, cannabichromene, cannabicyclol, cannabivarin, cannabielsoin, cannabicitran, cannabigerolic acid, cannabigerolic acid monomethylether, cannabigerol monomethylether, cannabigerovarinic acid, cannabigerovarin, cannabichromenic acid, cannabichromevarinic acid, cannabichromevarin, cannabidolic acid, cannabidiol monomethylether, cannabidiol-C4, cannabidivarinic acid, cannabidiorcol, delta-9-tetrahydrocannabinolic acid A, delta-9-tetrahydrocannabinolic acid B, delta-9-tetrahydrocannabinolic acid-C4, delta-9-tetrahydrocannabivarinic acid, delta-9-tetrahydrocannabivarin, delta-9-tetrahydrocannabiorcolic acid, delta-9-tetrahydrocannabiorcol, delta-7-cis-iso-tetrahydrocannabivarin, delta-8-tetrahydrocannabinolic acid, delta-8-tetrahydrocannabinol, cannabicyclolic acid, cannabicyclovarin, cannabielsoic acid A, cannabielsoic acid B, cannabinolic acid, cannabinol methylether, cannabinol-C4, cannabinol-C2, cannabiorcol, 10-ethoxy-9-hydroxy-delta-6a-tetrahydrocannabinol, 8,9-dihydroxy-delta-6a-tetrahydrocannabinol, cannabitriolvarin, ethoxy-cannabitriolvarin, dehydrocannabifuran, cannabifuran, cannabichromanon, cannabicitran, 10-oxo-delta-6a-tetrahydrocannabinol, delta-9-cis-tetrahydrocannabinol, 3, 4, 5, 6-tetrahydro-7-hydroxy-alpha-alpha-2-trimethyl-9-n-propyl-2, 6-methano-2H-1-benzoxocin-5-methanol-cannabiripsol, trihydroxy-delta-9-tetrahydrocannabinol, and cannabinol. Examples of cannabinoids within the context of this disclosure include tetrahydrocannabinol and cannabidiol.

The term "endocannabinoid" refer to compounds including arachidonoyl ethanolamide (anandamide, AEA), 2-arachidonoyl ethanolamide (2-AG), 1-arachidonoyl ethanolamide (1-AG), and docosahexaenoyl ethanolamide (DHEA, synaptamide), oleoyl ethanolamide (OEA), eicsapentaenoyl ethanolamide, prostaglandin ethanolamide, docosahexaenoyl ethanolamide, linolenoyl ethanolamide, 5(Z),8(Z),11(Z)-eicosatrienoic acid ethanolamide (mead acid ethanolamide), heptadecanoul ethanolamide, stearoyl ethanolamide, docosaenoyl ethanolamide, nervonoyl ethanolamide, tricosanoyl ethanolamide, lignoceroyl ethanolamide, myristoyl ethanolamide, pentadecanoyl ethanolamide, palmitoleoyl ethanolamide, docosahexaenoic acid (DHA). Particularly preferred endocannabinoids are AEA, 2-AG, 1-AG, and DHEA.

Terpenoids a.k.a. isoprenoids, are a large and diverse class of naturally occurring organic chemicals similar to terpenes, derived from five-carbon isoprene units assembled and modified in a number of varying configurations. Most are multi-cyclic structures that differ from one another not only in functional groups but also in their basic carbon skeletons. Terpenoids are essential for plant metabolism, influencing general development, herbivory defense, pollination and stress response. These compounds have been extensively used as flavoring and scenting agents in cosmetics, detergents, food and pharmaceutical products. They also display multiple biological activities in humans, such as anti-inflammatory, anti-microbial, antifungal and antiviral.

Cannabis terpenoid profiles define the aroma of each plant and share the same precursor (geranyl pyrophosphate) and the same synthesis location (glandular trichomes) as phytocannabinoids. The terpenoids most commonly found in Cannabis extracts include: limonine, myrcene, alpha-pinene, linalool, beta-caryophyllene, caryophyllene oxide, nerolidol, and phytol. Terpenoids are mainly synthesized in two metabolic pathways: mevalonic acid pathway (a.k.a. HMG-CoA reductase pathway, which takes place in the cytosol) and MEP/DOXP pathway (a.k.a. The 2-C-methyl-D-erythritol 4-phosphate/1-deoxy-D-xylulose 5-phosphate pathway, non-mevalonate pathway, or mevalonic acid-independent pathway, which takes place in plastids). Geranyl pyrophosphate (GPP), which is used by Cannabis plants to produce cannabinoids, is formed by condensation of dimethylallyl pyrophosphate (DMAPP) and isopentenyl pyrophosphate (IPP) via the catalysis of GPP synthase. Alternatively, DMAPP and IPP are ligated by FPP synthase to produce farnesyl pyrophosphate (FPP), which can be used to produce sesquiterpenoids. Geranyl pyrophospliate (GPP) can also be converted into monoterpenoids by limonene synthase.

Some examples of terpenes, and their classification, are as follows. Hemiterpenes: Examples of hemiterpenes, which do not necessarily have an odor, are 2-methyl-1,3-butadiene, hemialboside, and hymenoside. [0086] Monoterpenes: pinene, a-pinene, β-pinene, cis-pinane, trans-pinane, cis-pinanol, trans-pinanol (Erman and Kane (2008) Chem. Biodivers. 5:910-919), limonene; linalool; myrcene; eucalyptol; a-phellandrene; β-phellandrene; a-ocimene; β-ocimene, cis-ocimene, ocimene, Δ-3-carene; fenchol; sabinene, borneol, isoborneol, camphene, camphor, phellandrene, a-phellandrene, a-terpinene, geraniol, linalool, nerol, menthol, myrcene, terpinolene, a-terpinolene, β-terpinolene, γ-terpinolene, Δ-terpinolene, α-terpineol, and trans-2-pinanol. Sesquiterpenes: caryophyllene, caryophyllene oxide, humulene, a-humulene, a-bisabolene; β-bisabolene; santalol; selinene; nerolidol, bisabolol; a-cedrene, β-cedrene, β-eudesmol, eudesm-7(11)-en-4-ol, selina-3,7(11)-diene, guaiol, valencene, a-guaiene, β-guaiene, Δ-guaiene, guaiene, farnesene, a-farnesene, β-farnesene, elemene, a-elemene, β-elemene, γ-elemene, Δ-elemene, germacrene, germacrene A, germacrene B, germacrene C, germacrene D, and germacrene E. Diterpenes: oridonin, phytol, and isophytol. Triterpenes: ursolic acid, oleanolic acid. Terpenoids, also known as isoprenoids, are a large and diverse class of naturally occurring organic chemicals similar to terpenes, derived from five-carbon isoprene units assembled and modified in a number of ways. Most are multicyclic structures that differ from one another not only in functional groups but also in their basic carbon skeletons. Plant terpenoids are used extensively for their aromatic qualities.

As used herein, the term "homologous" with regard to a contiguous nucleic acid sequence, refers to contiguous nucleotide sequences that hybridize under appropriate conditions to the reference nucleic acid sequence. For example, homologous sequences may have from about 70%-100, or more generally 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

The term, "operably linked," when used in reference to a regulatory sequence and a coding sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; poly-adenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific."

A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters. A "constitutive" promoter is a promoter which may be active under most environmental conditions or in most cell or tissue types.

Any inducible promoter can be used in some embodiments of the invention. See Ward et al. (1993) Plant Mol. Biol. 22:361-366. With an inducible promoter, the rate of transcription increases in response to an inducing agent. Exemplary inducible promoters include, but are not limited to: Promoters from the ACEI system that responds to copper; In2 gene from maize that responds to benzenesulfo-namide herbicide safeners; Tet repressor from Tn10; and the inducible promoter from a steroid hormone gene, the transcriptional activity of which may be induced by a glucocorticosteroid hormone are general examples (Schena et al. (1991) Proc. Natl. Acad. Sci. USA 88:0421).

As used herein, the term "transformation" or "genetically modified" refers to the transfer of one or more nucleic acid molecule(s) into a cell. A plant is "transformed" or "genetically modified" by a nucleic acid molecule transduced into the plant when the nucleic acid molecule becomes stably replicated by the plant. Such transformation may be transient or stable. As used herein, the term "transformation" or "genetically modified" encompasses all techniques by which a nucleic acid molecule can be introduced into, such as a plant.

The term "vector" refers to some means by which DNA, RNA, a protein, or polypeptide can be introduced into a host. The polynucleotides, protein, and polypeptide which are to be introduced into a host can be therapeutic or prophylactic in nature; can encode or be an antigen; can be regulatory in nature, etc. There are various types of vectors including virus, plasmid, bacteriophages, cosmids, and bacteria.

As is known in the art, different organisms preferentially utilize different codons for generating polypeptides. Such "codon usage" preferences may be used in the design of nucleic acid molecules encoding the proteins and chimeras of the invention in order to optimize expression in a particular host cell system.

An "expression vector" is nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette." In contrast, as described in the examples herein, a "cassette" is a polynucleotide containing a section of an expression vector of this invention. The use of the cassettes assists in the assembly of the expression vectors. An expression vector is a replicon, such as plasmid, phage, virus, chimeric virus, or cosmid, and which contains the desired polynucleotide sequence operably linked to the expression control sequence(s).

A polynucleotide sequence is operably linked to an expression control sequence(s) (e.g., a promoter and, optionally, an enhancer) when the expression control sequence controls and regulates the transcription and/or translation of that polynucleotide sequence.

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). Because of the degeneracy of nucleic acid codons, one can use various different polynucleotides to encode identical polypeptides. Table 1a, infra, contains information about which nucleic acid codons encode which amino acids.

Amino Acid Nucleic Acid Codons

| Amino Acid | Nucleic Acid Codons |
|---|---|
| Ala/A | GCT, GCC, GCA, GCG |
| Arg/R | CGT, CGC, CGA, CGG, AGA, AGG |
| Asn/N | AAT, AAC |

-continued

| Amino Acid | Nucleic Acid Codons |
|---|---|
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |

The term "plant" or "plant system" includes whole plants, plant organs, progeny of whole plants or plant organs, embryos, somatic embryos, embryo-like structures, protocorms, protocorm-like bodies (PLBs), and culture and/or suspensions of plant cells. Plant organs comprise, e.g., shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like). The invention may also include Cannabaceae and other *Cannabis* strains, such as *C. sativa* generally.

The term "expression," as used herein, or "expression of a coding sequence" (for example, a gene or a transgene) refers to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

The term "nucleic acid" or "nucleic acid molecules" include single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double stranded RNA), siRNA (small interfering RNA), mRNA (messenger RNA), miRNA (micro-RNA), hpRNA (hairpin RNA), tRNA (transfer RNA), whether charged or discharged with a corresponding acylated amino acid), and cRNA (complementary RNA). The term "deoxyribonucleic acid" (DNA) is inclusive of cDNA, genomic DNA, and DNA-RNA hybrids. The terms "nucleic acid segment" and "nucleotide sequence segment," or more generally "segment," will be understood by those in the art as a functional term that includes both genomic sequences, ribosomal RNA sequences, transfer RNA sequences, messenger RNA sequences, operon sequences, and smaller engineered nucleotide sequences that encoded or may be adapted to encode, peptides, polypeptides, or proteins.

The term "gene" or "sequence" refers to a coding region operably joined to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (down-stream) the coding region (open reading frame, ORF) as well as, where applicable, intervening sequences (i.e., introns) between individual coding regions (i.e., exons). The term "structural gene" as used herein is intended to mean a DNA sequence that is transcribed into mRNA which is then translated into a sequence of amino acids characteristic of a specific polypeptide.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hair-pinned, circular, and padlocked conformations.

As used herein with respect to DNA, the term "coding sequence," "structural nucleotide sequence," or "structural nucleic acid molecule" refers to a nucleotide sequence that is ultimately translated into a polypeptide, via transcription and mRNA, when placed under the control of appropriate regulatory sequences. With respect to RNA, the term "coding sequence" refers to a nucleotide sequence that is translated into a peptide, polypeptide, or protein. The boundaries of a coding sequence are determined by a translation start codon at the 5'-terminus and a translation stop codon at the 3'-terminus. Coding sequences include but are not limited to: genomic DNA; cDNA; EST; and recombinant nucleotide sequences.

The term "sequence identity" or "identity," as used herein in the context of two nucleic acid or polypeptide sequences, refers to the residues in the two sequences that are the same when aligned for maximum correspondence over a specified comparison window.

The term "recombinant" when used with reference, e.g., to a cell, or nucleic acid, protein, or vector, indicates that the cell, organism, nucleic acid, protein or vector, has been modified by the introduction of a heterologous nucleic acid or protein, or the alteration of a native nucleic acid or protein, or that the cell is derived from a cell so modified. Thus, for example, recombinant cells may express genes that are not found within the native (nonrecombinant or wild-type) form of the cell or express native genes that are otherwise abnormally expressed—over-expressed, under expressed or not expressed at all.

The terms "approximately" and "about" refer to a quantity, level, value or amount that varies by as much as 30%, or in another embodiment by as much as 20%, and in a third embodiment by as much as 10% to a reference quantity, level, value or amount. As used herein, the singular form "a," "an," and "the" include plural references unless the context clearly dictates otherwise.

As used herein, "heterologous" or "exogenous" in reference to a nucleic acid is a nucleic acid that originates from a foreign species, or is synthetically designed, or, if from the same species, is substantially modified from its native form in composition and/or genomic locus by deliberate human intervention. A heterologous protein may originate from a foreign species or, if from the same species, is substantially modified from its original form by deliberate human intervention. By "host cell" is meant a cell which contains an introduced nucleic acid construct and supports the replication and/or expression of the construct.

Each publication or patent cited herein is incorporated herein by reference in its entirety. The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention. Indeed, while this invention has been particularly shown and described with references to preferred embodiments thereof, it will be understood by those skilled in the art that various changes in form and details may be made therein without departing from the scope of the invention encompassed by the appended claims

EXAMPLES

Example 1: Heterologous Expression of aaMYB in Hemp

Figure 8:
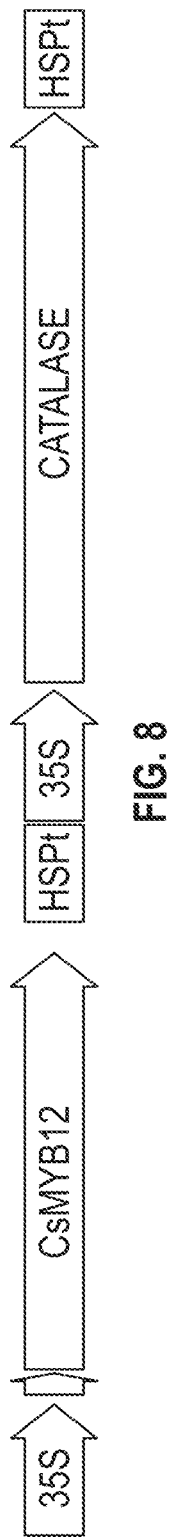
FIG. 8: Gene construct used to boost cannabinoid production. CsMYB12, predicted Cannabis sativa MYB transcription factor for enhancing flavonol biosynthesis; HSPt, efficient transcription terminator from the *Arabidopsis thaliana* heat shock protein 18.2 gene; 35S, constitutive promoter from cauliflower mosaic virus; Catalase, *Arabidopsis thaliana* catalase gene.
Figure 9:
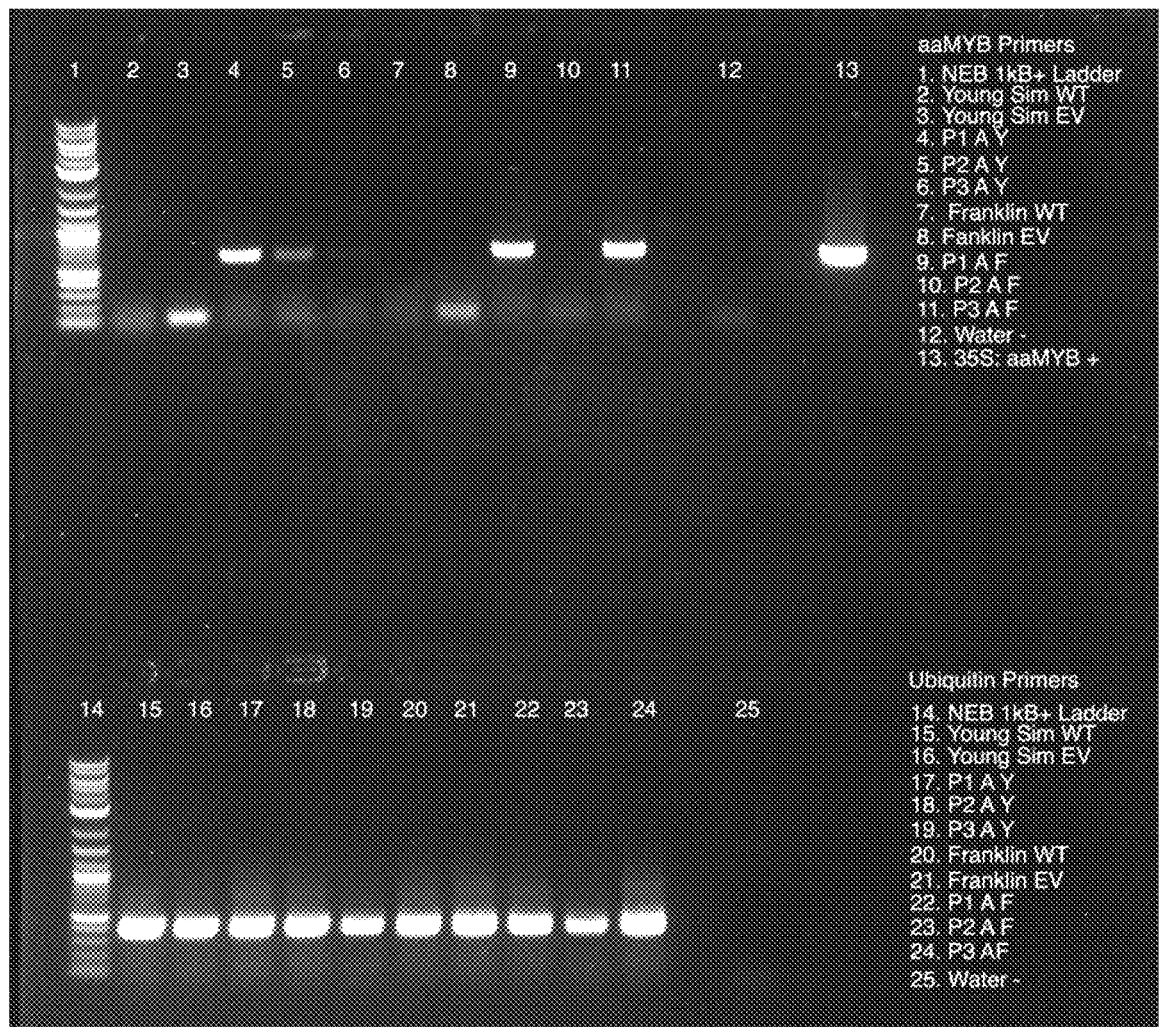
FIG. 9: Gene expression analysis in transgenic hemp plants overexpressing the *Artemisia annua* MYB transcription factor (aaMYB). Ubiquitin was used as the housekeeping control.
Figure 10A:
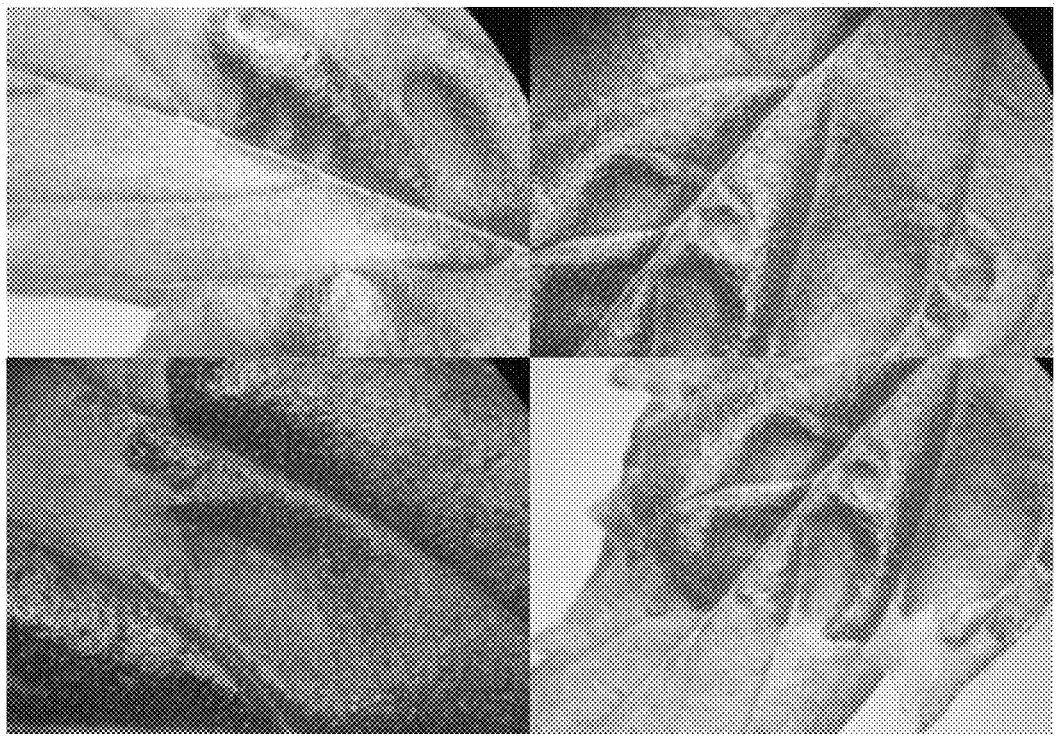
FIG. 10A-B: (A) Youngism10 hemp leaves 9 days post vacuum infiltration with 35s-*Artemisia annua* aaMYB1 in AGL1 *Agrobacterium*. Infiltrated leaves qualitatively demonstrate increased formation and density of trichome formation. (B) Youngism10 hemp leaves 9 days post vacuum infiltration with empty vector control.
Figure 10B:
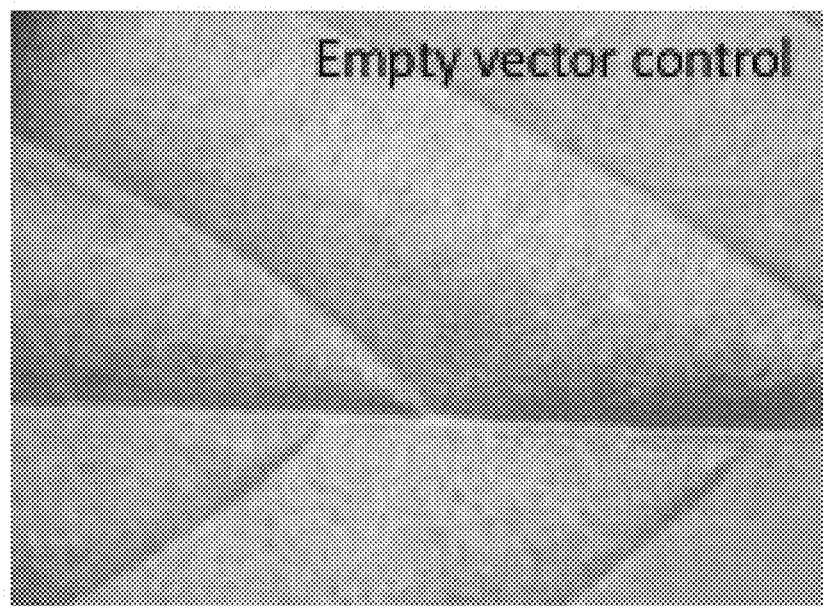

As generally shown in FIG. 8, hemp plants were infiltrated with *Agrobacterium tumefaciens* AGL1 strains harboring 35S-aaMYB1-pRI201 and the empty vector containing no aaMYB transgene optimized for expression in *Cannabis*. (nucleotide sequence SEQ ID NO. 6 amino acid sequence SEQ ID NO. 7). Expression of the transgene was confirmed in 3 transgenic lines for each cultivar.

Example 2: Enhanced Cannabinoid Biosynthesis in Transgenic Lines Overexpressing aaMYB As generally shown in table 1 below, overexpression of aaMYB in *Cannabis* resulted in up to 1.8-fold increase in total cannabinoid concentration relative to the empty vector in the cultivar Franklin (Table 1). Notably, THCA and CBDA in these lines increased 4 and 3-fold respectively. These results suggest that this MYB transcription factor enhances overall cannabinoid capacity, for example through enhanced biosynthesis, as well as enhanced trichome formation, density, and/or size.

Example 3: Stable Transformation and Expression of aaMYB

As shown in FIG. 7, a binary expression vector for overexpressing aaMYB1 was designed and constructed in the commercial vector pRI201-AN, a binary vector for high-level expression of a foreign gene in dicotyledonous plants carrying the constitutive 35S promoter and an *Arabidopsis* Alcohol dehydrogenase (AtAdh) as a translational enhancer. This construct used to generate stably transformed *Cannabis* plants expressing aaMYB1. The present inventors then overexpressed aaMYB to enhance trichome density in *Cannabis*/hemp and analyzed the plants for increased trichome formation, size and density as well as overall increase in production of cannabinoids.

Figure 11:
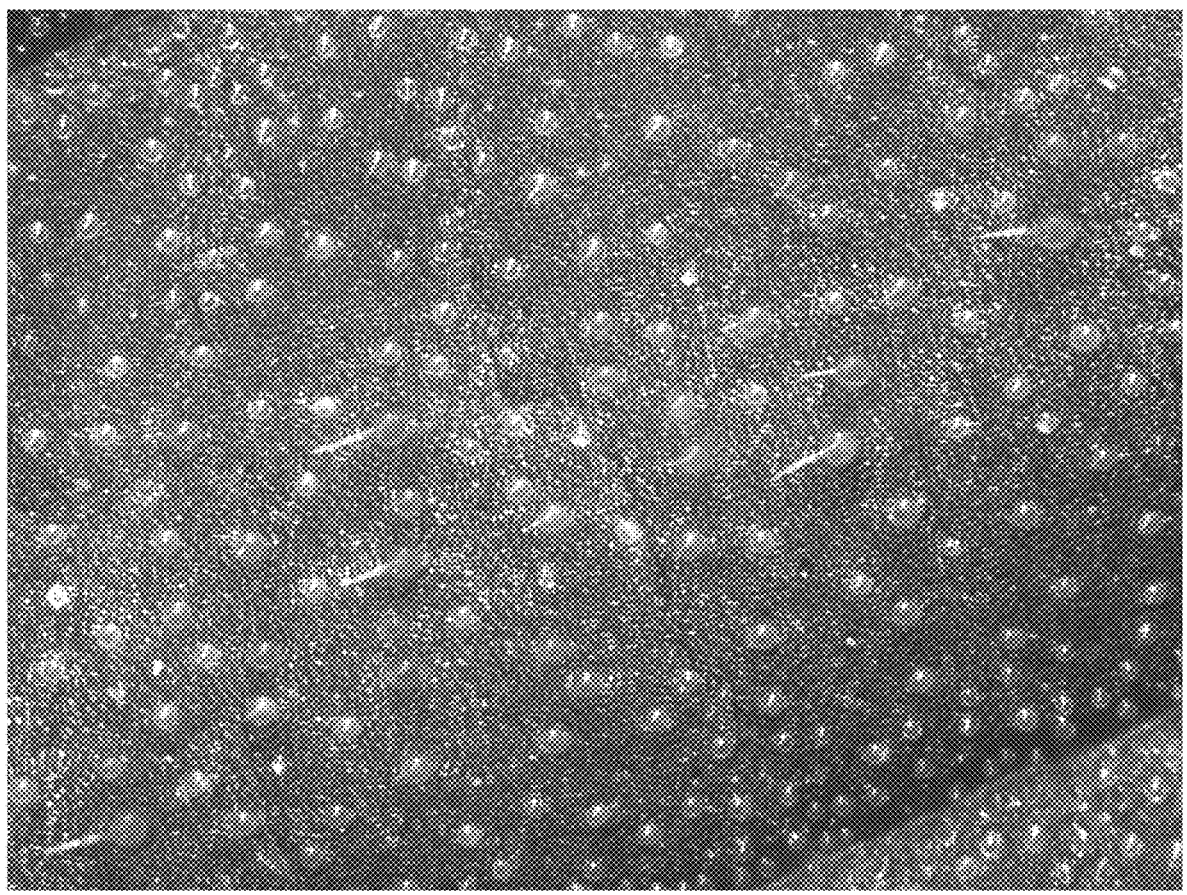
FIG. 11: Example of trichome image used in quantitative counting trichomes. Image demonstrates stably transformed *cannabis*/hemp plant expressing *Artemisia annua* aaMYB1. Trichomes were counted in an area of 234 cm2.

Example 4: Stable Transgenic Plants Overexpressing aaMYB1 Displayed Higher Average Number of Trichomes Structures As shown in FIG. 11, stably transformed *Cannabis* plants expressing aaMYB1 was generated and examined for enhance trichome formation phenotypes. Three fresh leaflets, approximately 10×2 mm, were harvested from each stably transformed plant. Leaflets were imaged using a Leica EZ40 dissecting scope at 35 times magnification. Leica EZ software was used to capture the selected images (FIG. 11). This image was imported into ImageJ and the multi-point tool was used to mark the trichomes counted to prevent double-counting or omitting trichomes. The number of trichomes on the three leaflets of a single plant was averaged.

Figure 12A:
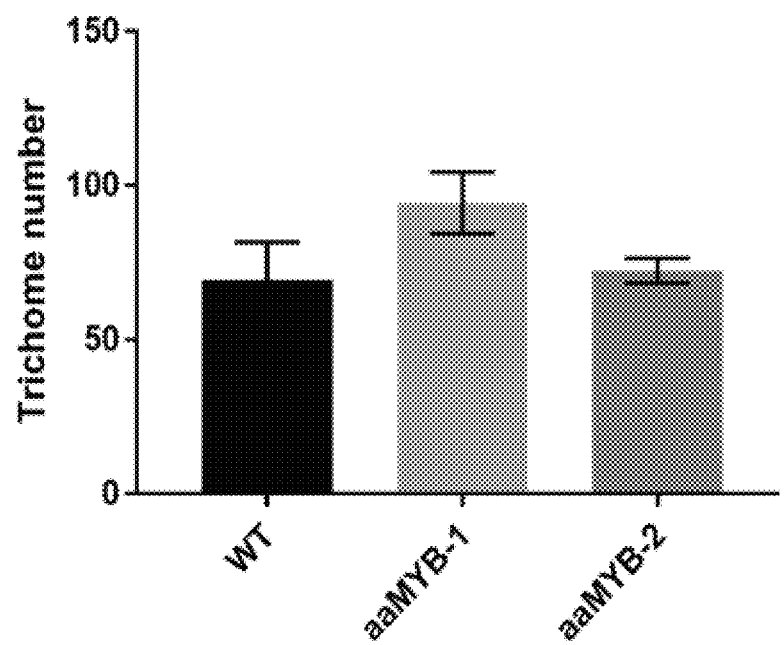
FIG. 12A-B: Stable transgenic *cannabis* plants overexpressing aaMYB1 displayed higher average number of trichomes per unit area. P1 transgenic plant, which presented the highest expression of aaMYB1 (B) had also significantly higher number of trichomes compared to the wild type (A).
Figure 12B:
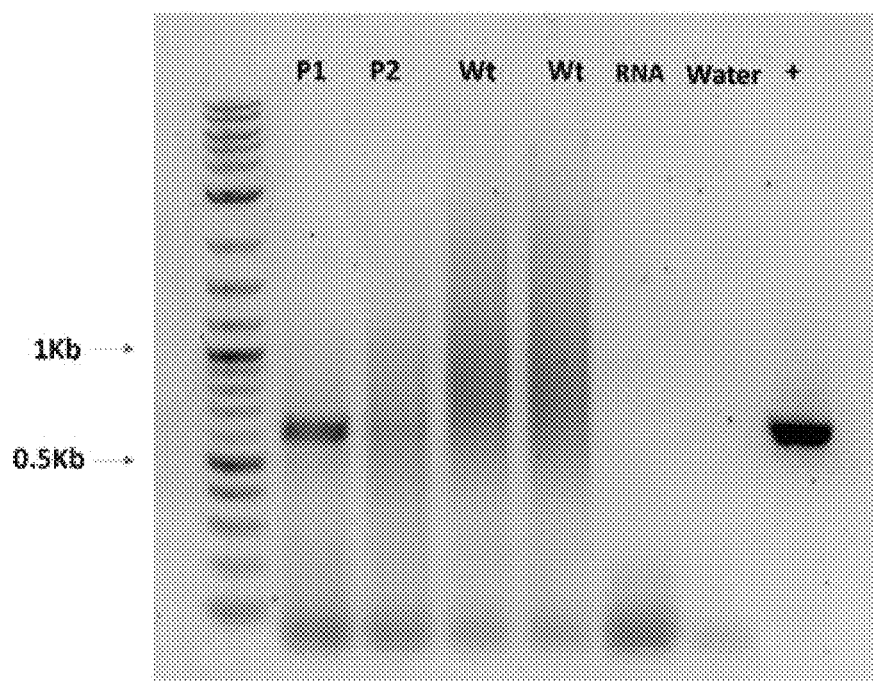

As shown in FIG. 12A-B, stable transgenic *Cannabis* plants overexpressing the *Artemisia annua* MYB transcription factor (aaMYB) demonstrated more trichomes than wild type plants. The average number of trichomes per unit area was 69.6 in wild-type plants, compared to 94.3 and 72.3 in the two independent transgenic lines (FIG. 12A-B). The transgenic lines with higher expression of the MYB transcription factor (aaMYB-1) had up to 35% more trichomes relative to the wild-type.

Example 5: Materials and Methods

Transformation of hemp. *Agrobacterium tumefaciens* AGL1 strains harboring 35S-aaMYB1-pRI201 and the empty vector (pRI201) were grown to an OD600 of ~0.8 in LB media. Cells were harvested by centrifugation and resuspended in vir induction medium (M9 minimal salts, 0.2% glucose, 10 mM MES pH5.2, 0.1 mM CaCl2, 2 mM MgSO4, 0.1 mM acetosyringone). Bacterial cells were further cultured by shaking overnight. Cells were pelleted and resuspended to an OD600 of 1 in infiltration media (10 mM MgCl2, 10 mM MES pH 5.2, 0.15 mM Acetosyringone). Three-week old Franklin and youngsim10 plants were vacuum infiltrated and kept in a moist chamber overnight. Five days after infiltration, leaf disks were collected for RNA and mass spec analyses. Expression of transgene was confirmed 2-3 days after infiltration by RT-PCR. For RT-PCR analysis, 100 mg of leaf tissue were frozen in liquid nitrogen and ground in a TissueLyser (QIAGEN Inc, USA). RNA was extracted following the EZNA plant RNA extraction kit (Omega Bio-tek Inc, USA). Up to a microgram of total RNA was used to synthesize cDNA using the superscript III cDNA synthesis kit (Thermo Fisher Scientific, USA). The cDNA was used to check for the expression of transgenes by RT-PCR.

Sample preparation. Leaf discs were lyophilized until fully dry, approximately 4 hr. Dry weights were recorded, and leaf discs were placed in 2.0 mL centrifuge tubes containing approximately 0.1 mL of 0.5 mm silica beads and ground in liquid nitrogen using a micropestle. Five volumes of 80% ethanol were added, and leaf disc samples were homogenized in the TissueLyzer at 50 oscillations/second for 5 minutes. Samples were centrifuged (15,000 rpm×2 min×room temperature) to clear cell debris, and approximately half of extraction volume was transferred to a clean 2.0 mL centrifuge tube. Extracts were centrifuged (15,000 rpm×2 min×room temperature) to clear any cell debris carried over. Samples were then diluted 1:50 in 70% methanol with 0.1% formic acid and 0.2 ppm 7-hydroxycoumarin as an internal standard for LC-MS/MS.

LC-MS/MS analysis. Separations were carried out using a Waters HSS T3 C18 column (300 µm×150 mm, particle size 1.8 µm) equipped to a Waters M-Class ACQUITY UPLC System, with a 1 µL injection volume and 5.0 µL/min flow rate. Mobile solvents (A) acetonitrile with 0.1% formic acid and (B) water with 0.1% formic acid were used for a linear gradient as follows: initial conditions 85:15% (ATM) for 2 minutes, linear ramp to 15:85% in 12 min, hold at 15:85% for 3.5 min, then equilibrate back to initial conditions 85:15% for 6.5 min and a total run time of 22 min, A LockMass solution of 0.5 nmol/mL leucine enkephalin (554.2615 m/z) was infused through an auxiliary pump at a flow rate of 5.0 µL/min to maintain mass accuracy.

Data were acquired in negative ionization mode (ES−) using a data-independent acquisition (MSe) method in continuum mode. Sample and lockspray capillary voltages were set to 2.0 and 2.5 kV, respectively, and sample cone and cone offset were set to 30 V each. MS acquisition was performed from 0.0-22.0 minutes over a mass range of 100-1200 m/z with a 0.486 s scan time with 0.014 s interscan delay. A high energy collision ramp of 5-30 V was applied, and LockSpray measurements were acquired every 30 s. All data processing steps, including metabolite identification, quantitation and LockMass correction, were performed in MassLynx using QuanLynx.

Stock solutions of analytical grade THC, MICA, CBD, CBDA, CBCA and CBGA standards were prepared in methanol with 0.2 ppm 7-hydroxycoumarin. CBD and THC were prepared at 10 µg/mL and CBDA, CBCA, CBGA and THCA at 1 µg/mL. Serial dilutions 2.5, 1.25, 0.625, 0.312, 0.156, 0.078, 0.039, 0.019, and 0.010 µg/mL) were prepared and analyzed using the LC-MS/MS method above to generate a calibration curve for quantitation of CBD, CBDA, CBGA, THC and THCA.

REFERENCES

The following references are hereby incorporated in their entirety by reference:

[1] I von Ossowski, M R Mulvey, P A Leco, A Borys and P C Loewen, *J Bacteriol.* 1991, 173(2):514.

[2] Behera, A., Behera, A., Mishra, S. C., Swain, S. K., & Author, C. (2003). Cannabinoid glycosides: In vitro production of a new class of cannabinoids with improved physicochemical properties. *Proc. Intl. Soc. Mag. Reson. Med* (Vol. 14).

[3] Holland, M. L., Lau, D. T. T., Allen, J. D., & Arnold, J. C. (2009). The multidrug transporter ABCG2 (BCRP) is inhibited by plant-derived cannabinoids. *British Journal of Pharmacology*, 152(5), 815-824. https://doi.org/10.1038/sj.bjp.0707467

[4] Ivanchenco. M., Vejlupkova. Z., Quatrano. R. S., Fowler. J. E. (2000) Maize ROP7 GTPase contains a unique, CaaX box-independent plasma membrane targeting signal. *The Plant Journal*, (24)1, 79-90.

[5] James M. Rini and Jeffrey D. Esko. Glycosyltransferases and Glycan-Processing Enzymes. In: Essentials of Glycobiology [Internet]. 3rd edition. https://www.ncbi.nlm.nih.gov/books/NBK310274/?report=reader

[6] Marks, M. D., Tian, L., Wenger, J. P., Omburo, S. N., Soto-Fuentes, W., He, J., . . . Dixon, R. A. (2009). Identification of candidate genes affecting Δ9-tetrahydrocannabinol biosynthesis in *Cannabis sativa*. *Journal of Experimental Botany*, 60(13), 3715-3726. https://doi.org/10.1093/jxb/erp210

[7] Nagaya, S., Kawamura, K., Shinmyo, A., & Kato, K. (2010). The HSP terminator of *Arabidopsis thaliana* increases gene expression in plant cells. *Plant and Cell Physiology*, 51(2), 328-332. https://doi.org/10.1093/pcp/pcp188

[8] Norambuena, L., Marchant, L., Berninsone, P., Hirschberg, C. B., Silva, H., & Orellana, A. (2002). Transport of UDP-galactose in plants. Identification and functional characterization of AtUTr1, an *Arabidopsis thaliana* UDP-galactose/UDP-glucose transporter. *Journal of Biological Chemistry*, 277(36), 32923-32929. https://doi.org/10.1074/jbc.M204081200

[9] Onofri, C., De Meijer, E. P. M., & Mandolino, G. (2015). Sequence heterogeneity of cannabidiolic- and tetrahydrocannabinolic acid-synthase in *Cannabis sativa* L. and its relationship with chemical phenotype. *Phytochemistry*, 116(1), 57-68. https://doi.org/10.1016/j.phytochem.2015.03.006

[9] Priest, D. M., Ambrose, S. J., Vaistij, F. E., Elias, L., Higgins, G. S., Ross, A. R. S., . . . Bowles, D. J. (2006). Use of the glucosyltransferase UGT71B6 to disturb abscisic acid homeostasis in *Arabidopsis thaliana*. *Plant Journal*, 46(3), 492-502. https://doi.org/10.1111/j.1365-313X.2006.02701.x

[10] Siritunga, D., and Sayre, R. T. (2003). Generation of cyanogen-free transgenic cassava. Planta 217, 367-373. doi: 10.1007/s00425-003-1005-8

[11] Sparkes, I. A., Runions, J., Kearns, A., & Hawes, C. (2006). Rapid, transient expression of fluorescent fusion proteins in tobacco plants and generation of stably transformed plants. *Nature Protocols*, 1(4), 2019-2025. https://doi.org/10.1038/nprot.2006.286

[13] Taura, F., Morimoto, S., & Shoyama, Y. (1996). Purification and characterization of cannabidiolic-acid synthase from *Cannabis sativa* L. Biochemical analysis of a novel enzyme that catalyzes the oxidocyclization of. *Journal of Biological Chemistry*, 271(29), 17411-17416. https://doi.org/10.1074/JBC.271.29.17411

[14] Taura, F., Sirikantaramas, S., Shoyama Y, Yoshikai K, Shoyama Y, Morimoto S. (2007) Cannabidiolic-acid synthase, the chemotype-determining enzyme in the fiber-type *Cannabis sativa*. *Febbs letters*, 581(16), 2929-34. DOI:10.1016/j.febslet.2007.05.043

[15] Yoo, S. D., Cho, Y. H., & Sheen, J. (2007). *Arabidopsis* mesophyll protoplasts: A versatile cell system for transient gene expression analysis. *Nature Protocols*, 2(7), 1565-1572. https://doi.org/10.1038/nprot.2007.199

[16] Matsui, T., Matsuura, H., Sawada, K., Takita, E., Kinjo, S., Takenami, S., . . . Kato, K. (2012). High level expression of transgenes by use of 5'-untranslated region of the *Arabidopsis thaliana* arabinogalactan-protein 21 gene in dicotyledons. *Plant Biotechnology*, 29(3), 319-322. https://doi.org/10.5511/plantbiotechnology.12.0322a

[17] Murashige, T., and Skoog, F. (1962). A revised medium for rapid growth and bioassays with tobacco tissue culture. Physiol. Plant. 15, 473-497. doi: 10.1111/j.1399-3054.1962.tb08052.x

[18] Zipp, et al., *Cannabinoid glycosides*: In vitro production of a new class of cannabinoids with improved physicochemical properties. bioRxiv preprint doi: http://dx.doi.org/10.1101/104349

[19] Mohamed, E. A., T. Iwaki, I. Munir, M. Tamoi, S. Shigeoka, and A. Wadano. 2003. Overexpression of bacterial catalase in tomato leaf chloroplasts enhances photooxidative stress tolerance. Plant Cell Environ. 26:2037-2046.

[20] Akhtar, M. T., 2013, Doctoral Thesis, Leiden University. Cannabinoids and zebrafish. 2013-05-22. http://hdl.handle.net/1887/20899

[21] Sayed Farag. Cannabinoids production in *Cannabis sativa* L.: An in vitro approach. Thesis • January 2014. DOI: 10.17877/DE290R-16298

[21] K, Watanabe, et al., Cytochrome P450 enzymes involved in the metabolism of tetrahydrocannabinols and cannabinol by human hepatic microsomes. Life Sciences. Volume 80, Issue 15, 20 Mar. 2007, Pages 1415-1419

[22] Flores-Sanchez IJ. et al., Elicitation studies in cell suspension cultures of *Cannabis sativa* L. J Biotechnol. 2009 Aug. 20; 143(2):157-68. doi: 10.1016/j jbiotec.

[23] Stephen M. Stout & Nina M. Cimino (2013) Exogenous cannabinoids as substrates, inhibitors, and inducers of human drug metabolizing enzymes: a systematic review, Drug Metabolism Reviews, 46:1, 86-95, DOI: 10.3109/03602532.2013.849268

[24] Andre CM, Hausman J-F, Guerriero G. *Cannabis sativa*: The Plant of the Thousand and One Molecules. Frontiers in Plant Science. 2016; 7:19. doi:10.3389/fpls.2016.00019.

[25] Mahlberg Pl. et al., Accumulation of Cannabinoids in Glandular Trichomes of *Cannabis* (Cannabaceae). Journal of Industrial Hemp 9(1):15-36 • June 2004 with 273 Reads DOI: 10.1300/J237v09n01_04.

[25] Katalin S., et al., Mini Rev Med Chem. 2017; 17(13): 1223-1291. doi: 10.2174/1389557516666161004162133.

[26] Sirikantaramas S., et al., Tetrahydrocannabinolic Acid Synthase, the Enzyme Controlling Marijuana Psychoactivity, is Secreted into the Storage Cavity of the Glandular Trichomes. Plant and Cell Physiology, Volume 46, Issue 9, 1 Sep. 2005, Pages 1578-1582, https://doi.org/10.1093/pcp/pci166.

[26] Schilmiller A L, Last R L, Pichersky E (2008) Harnessing plant trichome biochemistry for the production of useful compounds. Plant Journal 54: 702-711.

[27] Fellermeier, M., Eisenreich, W., Bacher, A., & Zenk, M. H. (2001). Biosynthesis of cannabinoids. European Journal of Biochemistry, 268(6), 1596-1604. https://doi.org/10.1046/j.1432-1327.2001.02030.x

[28] Matías-Hernández, L., Jiang, W., Yang, K., Tang, K., Brodelius, P. E., & Pelaz, S. (2017). AaMYB1 and its orthologue AtMYB61 affect terpene metabolism and trichome development in *Artemisia annua* and *Arabidopsis thaliana*. Plant Journal, 90(3), 520-534. https://doi.org/10.1111/tpj 0.13509

[29] Matsui, T., Matsuura, H., Sawada, K., Takita, E., Kinjo, S., Takenami, S., . . . Kato, K. (2012). High level expression of transgenes by use of 5'-untranslated region of the *Arabidopsis thaliana* arabinogalactan-protein 21 gene in dicotyledons. Plant Biotechnology. https://doi.org/10.5511/plantbiotechnology.12.0322a

[30] Nagaya, S., Kawamura, K., Shinmyo, A., & Kato, K. (2017). The HSP Terminator of *Arabidopsis thaliana* Increases Gene Expression in Plant Cells, 51(2), 328-332. https://doi.org/10.1093/pcp/pcp188

[31] Sirikantaramas, S., Taura, F., Tanaka, Y., Ishikawa, Y., Morimoto, S., & Shoyama, Y. (2005). Tetrahydrocannabinolic acid synthase, the enzyme controlling marijuana psychoactivity, is secreted into the storage cavity of the glandular trichomes. Plant and Cell Physiology, 46(9), 1578-1582. https://doi.org/10.1093/pcp/pci166

[32] Marks, M. D., Tian, L., Wenger, J. P., Omburo, S. N., Soto-Fuentes, W., He, J., Dixon, R. A. (2009). Identification of candidate genes affecting $\Delta^9$-tetrahydrocannabinol biosynthesis in *Cannabis sativa*. *Journal of Experimental Botany*, 60(13), 3715-3726. http://doi.org/10.1093/jxb/erp210

[33] Matias-Hernández, et al., (2017), AaMYB1 and its orthologue AtMYB61 affect terpene metabolism and trichome development in *Artemisia annua* and *Arabidopsis thaliana*. The Plant Journal, 90: 520-534. doi: 10.1111/tpj.13509

[34] Taura, Futoshi, et al., (2007) Cannabidiolic-acid synthase, the chemotype-determining enzyme in the fiber-type *Cannabis sativa*. Feb Letters Volume 581, Issue 16: 2929-2934

[35] Andre, C. M., Hausman, J.-F., & Guerriero, G. (2016). *Cannabis sativa*: The Plant of the Thousand and One Molecules. Frontiers in Plant Science, 7(February), 1-17. https://doi.org/10.3389/fpls.2016.00019

[36] Booth, J. K., Page, J. E., & Bohlmann, J. (2017). Terpene synthases from *Cannabis sativa*. PLoS ONE, 12(3). https://doi.org/10.1371/journal.pone.0173911

[36] Comai, L., Moran, P., & Maslyar, D. (1990). Novel and useful properties of a chimeric plant promoter combining CaMV 35S and MAS elements. Plant Molecular Biology, 15(3), 373-381. https://doi.org/10.1007/BF00019155

Tables

TABLE 1

Cannabinoid concentrations in aaMYB transgenic lines relative to empty vector controls.

| Plant | Concentration THC/THCA (mg/L)[1] | Concentration CBD/CBDA (mg/L)[1] | Concentration CBC/CBCA (mg/L)[1] | Concentration Total Cannabinoids (mg/L)[1] |
|---|---|---|---|---|
| aaMyb Franklin | 1.75 ± 0.64 | 28.51 ± 8.37 | 15.44 ± 1.01 | 45.69 ± 8.26 |
| Empty Vector Franklin | 0.43 ± 0.14 | 8.95 ± 2.06 | 16.11 ± 1.95 | 25.50 ± 3.64 |
| aaMyb Youngsim | 4.15 ± 0.49 | 66.68 ± 5.16 | 8.79 ± 2.13 | 79.61 ± 7.77 |
| Empty Vector Youngsim | 2.91 ± 0.47 | 52.61 ± 3.16 | 7.43 ± 2.04 | 62.94 ± 3.11 |

Sequence Listings

As noted above, the instant application contains a full Sequence Listing which has been submitted electronically in ASCII format and is hereby incorporated by reference in its entirety. The following sequences are further provided herewith and are hereby incorporated into the specification in their entirety:

```
DNA
MYB12-like
Cannabis
                                                         SEQ ID NO. 1
ATGAAGAAGAACAAATCAACTAGTAATAATAAGAACAACAACAGTAATAATATCATCAAAAACG

ACATCGTATCATCATCATCATCAACAACAACAACATCATCAACAACTACAGCAACATCATCATT

TCATAATGAGAAAGTTACTGTCAGTACTGATCATATTATTAATCTTGATGATAAGCAGAAACGA

CAATTATGTCGTTGTCGTTTAGAAAAAGAAGAAGAAGAAGAAGGAAGTGGTGGTTGTGGTGAGA

CAGTAGTAATGATGCTAGGGTCAGTATCTCCTGCTGCTGCTACTGCTGCTGCAGCTGGGGGCTC

ATCAAGTTGTGATGAAGACATGTTGGGTGGTCATGATCAACTGTTGTTGTTGTGTTGTTCTGAG

AAAAAAACGACAGAAATTTCATCAGTGGTGAACTTTAATAATAATAATAATAATAATAAGGAAA

ATGGTGACGAAGTTTCAGGACCGTACGATTATCATCATCATAAAGAAGAGGAAGAAGAAGAAGA

AGAAGATGAAGCATCTGCATCAGTAGCAGCTGTTGATGAAGGGATGTTGTTGTGCTTTGATGAC

ATAATAGATAGCCACTTGCTAAATCCAAATGAGGTTTTGACTTTAAGAGAAGATAGCCATAATG

AAGGTGGGGCAGCTGATCAGATTGACAAGACTACTTGTAATAATACTACTATTACTACTAATGA

TGATTATAACAATAACTTGATGATGTTGAGCTGCAATAATAACGGAGATTATGTTATTAGTGAT

GATCATGATGATCAGTACTGGATAGACGACGTCGTTGGAGTTGACTTTTGGAGTTGGGAGAGTT

CGACTACTACTGTTATTACCCAAGAACAAGAACAAGAACAAGATCAAGTTCAAGAACAGAAGAA

TATGTGGGATAATGAGAAAGAGAAACTGTTGTCTTTGCTATGGGATAATAGTGATAACAGCAGC

AGTTGGGAGTTACAAGATAAAAGCAATAATAATAATAATAATAATGTTCCTAACAAATGTCAAG

AGATTACCTCTGATAAAGAAAATGCTATGGTTGCATGGCTTCTCTCCTGA

Amino Acid
MYB12
Cannabis
                                                         SEQ ID NO. 2
MKKNKSTSNNKNNNSNNIIKNDIVSSSSSTTTTSSTTTATSSFHNEKVTVSTDHIINLDDKQKR

QLCRCRLEKEEEEGSGGCGETVVMMLGSVSPAAATAAAAGGSSSCDEDMLGGHDQLLLLCCSE

KKTTEISSVVNFNNNNNNNKENGDEVSGPYDYHHHKEEEEEEEEDEASASVAAVDEGMLLCFDD

IIDSHLLNPNEVLTLREDSHNEGGAADQIDKTTCNNTTITTNDDYNNNLMMLSCNNNGDYVISD
```

-continued

DHDDQYWIDDVVGVDFWSWESSTTTVITQEQEQEQDQVQEQKNMWDNEKEKLLSLLWDNSDNSS

SWELQDKSNNNNNNNNVPNKCQEITSDKENAMVAWLLS

Amino Acid
MYB8-orthologue for CAN738
*Humulus lupulus*
SEQ ID NO. 3
MGRAPCCEKVGLKKGRWTSEEDEILTKYIQSNGEGCWRSLPKNAGLLRCGKSCRLRWINYLRAD

LKRGNISSEEEDIIIKLHSTLGNRWSLIASHLPGRTDNEIKNYWNSHLSRKIHTFRRCNNTTTH

HHHLPNLVTVTKVNLPIPKRKGGRTSRLAMKKNKSSTSNQNSSVIKNDVGSSSSTTTTSVHQRT

TITTPTMDDQQKRQLSRCRLEEKEDQDGASTGTVVMMLGQAAAVGSSCDEDMLGHDQLSFLCCS

EEKTTENSMTNLKENGDHEVSGPYDYDHRYEKETSVDEGMLLCFNDIIDSNLLNPNEVLTLSEE

SLNLGGALMDTTTSTTTNNNNYSLSYNNNGDCVISDDHDQYWLDDVVGVDFWSWESSTTVTQEQ

EQEQEQEQEQEQEQEQEHHHQQDQKKNTWDNEKEKMLALLWDSDNSNWELQDNNNYHKCQEI

TSDKENAMVAWLLS

Amino Acid
atMYB12-orthologue for CAN739
*Arabidopsis thaliana*
SEQ ID NO. 4
MGRAPCCEKVGIKRGRWTAEEDQILSNYIQSNGEGSWRSLPKNAGLKRCGKSCRLRWINYLRSD

LKRGNITPEEEELVVKLHSTLGNRWSLIAGHLPGRTDNEIKNYWNSHLSRKLHNFIRKPSISQD

VSAVIMTNASSAPPPPQAKRRLGRTSRSAMKPKIHRTKTRKTKKTSAPPEPNADVAGADKEALM

VESSGAEAELGRPCDYYGDDCNKNLMSINGDNGVLTFDDDIIDLLLDESDPGHLYTNTTCGGDG

ELHNIRDSEGARGFSDTWNQGNLDCLLQSCPSVESFLNYDHQVNDASTDEFIDWDCVWQEGSDN

NLWHEKENPDSMVSWLLDGDDEATIGNSNCENFGEPLDHDDESALVAWLLS

Amino Acid
MYB112-orthologue for CAN833
*Arabidopsis thaliana*
SEQ ID NO. 5
MNISRTEFANCKTLINHKEEVEEVEKKMEIEIRRGPWTVEEDMKLVSYISLHGEGRWNSLSRSA

GLNRTGKSCRLRWLNYLRPDIRRGDISLQEQFIILELHSRWGNRWSKIAQHLPGRTDNEIKNYW

RTRVQKHAKLLKCDVNSKQFKDTIKHLWMPRLIERIAATQSVQFTSNHYSPENSSVATATSSTS

SSEAVRSSFYGGDQVEFGTLDHMTNGGYWFNGGDTFETLCSFDELNKWLIQ

Amino Acid
*Artemisia annua* MYB1 transcription factor (aaMYB or aaMYB1)
SEQ ID NO. 6
MARHSTCYKQRLRKGLWSPEEDEKLIKHITKFGHGCWSSVPKLAGLQRCGKSCRLRWINYLRPD

LKRGTFSQQEETLIVELHAVLGNKWSQIAAQLPGRTDNEIKNLWNSSIKKKLRQRGIDPNTHKP

LSDVENEDKPSPRSNNKNHQQTIIPSIENPSLETHEFFRNRFTTSHENANLASHTDTKHNNTDQ

FSGFLDFAYNQPPQPESSLLFGSSSNTDTSLSNPFQPTNWDTTTSLFDANNGFHNQVPLVGNES

QPEDIKWNKYLQSPFMFGGATLQSRVLCNETKPDLGMSINMNMNINNELYGNHEGVDTYNKQLQ

RICASYGQFT

DNA
MYB1 transcription factor (aaMYB) codon optimized for expression
in *Cannabis sativa*
*Artemisia annua*
SEQ ID NO. 7
ATGGCTAGACATTCAACTTGCTATAAACAAAGATTGAGAAAAGGATTGTGGTCACCTGAAGAAG

ATGAAAAATTGATTAAACATATTACTAAATTTGGACATGGATGCTGGTCATCAGTTCCTAAATT

GGCTGGATTGCAAAGATGCGGAAAATCATGCAGATTGAGATGGATTAATTATTTGAGACCTGAT

TTGAAAAGAGGAACTTTTTCACAACAAGAAGAAACTTTGATTGTTGAATTGCATGCTGTTTTGG

```
-continued
GAAATAAATGGTCACAAATTGCTGCTCAATTGCCTGGAAGAACTGATAATGAAATTAAAAATTT

GTGGAATTCATCAATTAAAAAAAAATTGAGACAAAGAGGAATTGATCCTAATACTCATAAACCT

TTGTCAGATGTTGAAAATGAAGATAAACCTTCACCTAGATCAAATAATAAAAATCATCAACAAA

CTATTATTCCTTCAATTGAAAATCCTTCATTGGAAACTCATGAATTTTTTAGAAATAGATTTAC

TACTTCACATGAAAATGCTAATTTGGCTTCACATACTGATACTAAACATAATAATACTGATCAA

TTTTCAGGATTTTTGGATTTTGCTTATAATCAACCTCCTCAACCTGAATCATCATTGTTGTTTG

GATCATCATCAAATACTGATACTTCATTGTCAAATCCTTTTCAACCTACTAATTGGGATACTAC

TACTTCATTGTTTGATGCTAATAATGGATTTCATAATCAAGTTCCTTTGGTTGGAAATGAATCA

CAACCTGAAGATATTAAATGGAATAAATATTTGCAATCACCTTTTATGTTTGGAGGAGCTACTT

TGCAATCAAGAGTTTTGTGCAATGAAACTAAACCTGATTTGGGAATGTCAATTAATATGAATAT

GAATATTAATAATGAATTGTATGGAAATCATGAAGGAGTTGATACTTATAATAAACAATTGCAA

AGAATTTGCGCTTCATATGGACAATTTACTTAA

DNA
H1MYB8 gene for Humulus lupulus MYB8 transcription factor,
codon optimized for expression in Cannabis sativa
Humulus lupulus
                                                         SEQ ID NO. 8
ATGGGAAGAGCTCCTTGCTGCGAAAAAGTTGGATTGAAAAAAGGAAGATGGACTTCAGAAGAAG

ATGAAATTTTGACTAAATATATTCAATCAAATGGAGAAGGATGCTGGAGATCATTGCCTAAAAA

TGCTGGATTGTTGAGATGCGGAAAATCATGCAGATTGAGATGGATTAATTATTTGAGAGCTGAT

TTGAAAAGAGGAAATATTTCATCAGAAGAAGAAGATATTATTATTAAATTGCATTCAACTTTGG

GAAATAGATGGTCATTGATTGCTTCACATTTGCCTGGAAGAACTGATAATGAAATTAAAAATTA

TTGGAATTCACATTTGTCAAGAAAAATTCATACTTTTAGAAGATGCAATAATACTACTACTCAT

CATCATCATTTGCCTAATTTGGTTACTGTTACTAAAGTTAATTTGCCTATTCCTAAAAGAAAAG

GAGGAAGAACTTCAAGATTGGCTATGAAAAAAATAAATCATCAACTTCAAATCAAAATTCATC

AGTTATTAAAAATGATGTTGGATCATCATCATCAACTACTACTACTTCAGTTCATCAAAGAACT

ACTACTACTACTCCTACTATGGATGATCAACAAAAAAGACAATTGTCAAGATGCAGATTGGAAG

AAAAAGAAGATCAAGATGGAGCTTCAACTGGAACTGTTGTTATGATGTTGGGACAAGCTGCTGC

TGTTGCTGGATCATCATGCGATGAAGATATGTTGGGACATGATCAATTGTCATTTTTGTGCTGC

TCAGAAGAAAAACTACTGAAAATTCAATGACTAATTTGAAAGAAAATGGAGATCATGAAGTTT

CAGGACCTTATGATTATGATCATAGATATGAAAAAGAAACTTCAGTTGATGAAGGAATGTTGTT

GTGCTTTAATGATATTATTGATTCAAATTTGTTGAATCCTAATGAAGTTTTGACTTTGTCAGAA

GAATCATTGAATTTGGGAGGAGCTTTGATGGATACTACTACTTCAACTACTACTAATAATAATA

ATTATTCATTGTCATATAATAATAATGGAGATTGCGTTATTTCAGATGATCATGATCAATATTG

GTTGGATGATGTTGTTGGAGTTGATTTTTGGTCATGGGAATCATCAACTACTGTTACTCAAGAA

CAAGAACAAGAACAAGAACAAGAACAAGAACAAGAACAAGAACAAGAACAAGAACAAGAACATC

ATCATCAACAAGATCAAAAAAAAAATACTTGGGATAATGAAAAGAAAAATGTTGGCTTTGTT

GTGGGATTCAGATAATTCAAATTGGGAATTGCAAGATAATAATAATTATCATAAATGCCAAGAA

ATTACTTCAGATAAAGAAAATGCTATGGTTGCTTGGTTGTTGTCATAA

DNA
atMYB12-orthologue for CAN739-transcription factor, codon-
optimized for expression in Cannabis sativa
Arabidopsis thaliana
                                                         SEQ ID NO. 9
ATGGGAAGAGCTCCTTGCTGCGAAAAAGTTGGAATTAAAAGAGGAAGATGGACTGCTGAAGAAG

ATCAAATTTTGTCAAATTATATTCAATCAAATGGAGAAGGATCATGGAGATCATTGCCTAAAAA
```

-continued

```
TGCTGGATTGAAAAGATGCGGAAAATCATGCAGATTGAGATGGATTAATTATTTGAGATCAGAT

TTGAAAAGAGGAAATATTACTCCTGAAGAAGAAGAATTGGTTGTTAAATTGCATTCAACTTTGG

GAAATAGATGGTCATTGATTGCTGGACATTTGCCTGGAAGAACTGATAATGAAATTAAAAATTA

TTGGAATTCACATTTGTCAAGAAAATTGCATAATTTTATTAGAAAACCTTCAATTTCACAAGAT

GTTTCAGCTGTTATTATGACTAATGCTTCATCAGCTCCTCCTCCTCCTCAAGCTAAAAGAAGAT

TGGGAAGAACTTCAAGATCAGCTATGAAACCTAAAATTCATAGAACTAAAACTAGAAAAACTAA

AAAAACTTCAGCTCCTCCTGAACCTAATGCTGATGTTGCTGGAGCTGATAAAGAAGCTTTGATG

GTTGAATCATCAGGAGCTGAAGCTGAATTGGGAAGACCTTGCGATTATTATGGAGATGATTGCA

ATAAAAATTTGATGTCAATTAATGGAGATAATGGAGTTTTGACTTTTGATGATGATATTATTGA

TTTGTTGTTGGATGAATCAGATCCTGGACATTTGTATACTAATACTACTTGCGGAGGAGATGGA

GAATTGCATAATATTAGAGATTCAGAAGGAGCTAGAGGATTTTCAGATACTTGGAATCAAGGAA

ATTTGGATTGCTTGTTGCAATCATGCCCTTCAGTTGAATCATTTTTGAATTATGATCATCAAGT

TAATGATGCTTCAACTGATGAATTTATTGATTGGGATTGCGTTTGGCAAGAAGGATCAGATAAT

AATTTGTGGCATGAAAAGAAAATCCTGATTCAATGGTTTCATGGTTGTTGGATGGAGATGATG

AAGCTACTATTGGAAATTCAAATTGCGAAAATTTTGGAGAACCTTTGGATCATGATGATGAATC

AGCTTTGGTTGCTTGGTTGTTGTCATAA
```

Amino Acid
AtMYB86
*Arabidopsis thaliana*
SEQ ID NO. 10

MGRHSCCFKQKLRKGLWSPEEDEKLLNYITRHGHGCWSSVPKLAGLQRCGKSCRLRWINYLRPD

LKRGAFSQDEESLIIELHAALGNRWSQIATRLPGRTDNEIKNFWNSCLKKKLRRKGIDPTTHKP

LITNELQSLNVIDQKLTSSEVVKSTGSINNLHDQSMVVSSQQGPWWFPANTTTTNQNSAFCFSS

SNTTTVSDQIVSLISSMSTSSSPTPMTSNFSPAPNNWEQLNYCNTVPSQSNSIYSAFFGNQYTE

ASQTMNNNNPLVDQHHHHQDMKSWASEILHYTEHNQSSETVIEAEVKPDIANYYWRSASSSSSP

NQEAATLLHDANVEVYGKNLQKLNNMVFDQSL

Amino Acid
AtMYB55
*Arabidopsis thaliana*
SEQ ID NO. 11

MGRHSCCYKQKLRKGLWSPEEDEKLLRYITKYGHGCWSSVPKQAGTFLFIQIHLLFGLQRCGKS

CRLRWINYLRPDLKRGAFSQDEENLIIELHAVLGNRWSQIAAQLPGRTDNEIKNLWNSCLKKKL

RLRGIDPVTHKLLTEIETGTDDKTKPVEKSQQTYLVETDGSSSTTTCSTNQNNNTDHLYTGNFG

FQRLSLENGSRIAAGSDLGIWIPQTGRNHHHHVDETIPSAVVLPGSMFSSGLTGYRSSNLGLIE

LENSFSTGPMMTEHQQIQESNYNNSTFFGNGNLNWGLTMEENQNPFTISNHSNSSLYSDIKSET

NFFGTEATNVGMWPCNQLQPQQHAYGHI

Amino Acid
AtMYB50
*Arabidopsis thaliana*
SEQ ID NO. 12

MGRHSCCYKQKLRKGLWSPEEDEKLLTHITNHGHGCWSSVPKLAGLQRCGKSCRLRWINYLRPD

LKRGAFSPEEENLIVELHAVLGNRWSQIASRLPGRTDNEIKNLWNSSIKKKLKQRGIDPNTHKP

ISEVESFSDKDKPTTSNNKRSGNDHKSPSSSSATNQDFFLERPSDLSDYFGFQKLNFNSNLGLS

VTTDSSLCSMIPPQFSPGNMVGSVLQTPVCVKPSISLPPDNNSSSPISGGDHVKLAAPNWEFQT

NNNNTSNFFDNGGFSWSIPNSSTSSSQVKPNHNFEEIKWSEYLNTPFFIGSTVQSQTSQPIYIK

SETDYLANVSNMTDPWSQNENLGTTETSDVFSKDLQRMAVSFGQSL

-continued

Amino Acid
AtMYB61
*Arabidopsis thaliana*
SEQ ID NO. 13

MKRHSCCYKQKLRKGLWSPEEDEKLLNYITKHGHGCWSSVPKLAGLERCGKSCRLRWINYLRPD

LKRGAFSSEEQNLIVELHAVLGNRWSQIAARLPGRTDNEIKNLWNSCIKKKLMKKGIDPITHKP

LSEVGKETNRSDNNNSTSFSSETNQDLFVKKTSDFAEYSAFQKEESNSVSLRNSLSSMIPTQFN

IDDGSVSNAGFDTQVCVKPSIILLPPPNNTSSTVSGQDHVNVSEPNWESNSGTTSHLNNPGMEE

MKWSEEYLNESLFSTQVYVKSETDFNSNIAFPWSQSQACDVFPKDLQRMAFSFGGQTL

Amino Acid
MYB8
*Humulus lupulus*
SEQ ID NO. 14

MGRAPCCEKVGLKKGRWTSEEDEILTKYIQSNGEGCWRSLPKNAGLLRCGKSCRLRWINYLRADLKRGNI

SSEEEDIIIKLHSTLGNRWSLIASHLPGRTDNEIKNYWNSHLSRKIHTFRRCNNTITHHHHHLPNLVTVIK

VNLPIPKRKGGRTSRLAMKKNKSSTSNQNSSVIKNDVGSSSSTITTSVHQRTTITTPTMDDQQKRQLSRC

RLEEKEDQDGASTGTVVMMLGQAAAVAGSSCDEDMLGHDQLSFLCCSEEKTTENSMTNLKENGDHEVSGP

YDYDHRYEKETSVDEGMLLCFNDIIDSNLLNPNEVLTLSEESLNLGGALMDTTTSTTTNNNNYSLSYNNN

GDCVISDDHDQYWLDDVVGVDFWSWESSTTVTQEQEQEQEQEQEQEQEQEHHHQQDQKKNTWDNEK

EKMLALLWDSDNSNWELQDNNNYHKCQEITSDKENAMVAWLLS

---

What is claimed is:

1. A method of increasing trichome formation in a plant comprising the steps:
stably transforming a *Cannabis* plant to express a heterologous polynucleotide sequence according to SEQ ID NO. 7, or a fragment thereof, wherein expression of the heterologous polynucleotide sequence upregulates trichome formation in said *Cannabis* plant.

2. The method of claim 1 wherein said *Cannabis* plant is *Cannabis sativa* or hemp.

3. The method of claim 2 wherein the nucleotide sequence SEQ ID NO. 7 is operably linked to a promoter to produce an expression vector and wherein said expression vector is configured to be introduced via transformation to a *Cannabis sativa* or hemp plant.

4. The method of claim 3 wherein the *Cannabis sativa* or hemp plant is stably transformed through *Agrobacterium* Ti-plasmid mediated transformation.

5. A genetically modified *Cannabis sativa* or hemp plant or part thereof produced by the method of claim 4.

6. A genetically modified *Cannabis sativa* or hemp plant or part thereof produced by the method of claim 3.

7. The genetically modified *Cannabis sativa* or hemp plant or part thereof and its progeny of claim 6 wherein the plant produces 30% more trichome structures compared to a wild-type *Cannabis sativa* or hemp plant.

8. The genetically modified *Cannabis sativa* or hemp plant or part thereof of claim 7 wherein its progeny is a seed from the genetically modified *Cannabis sativa* or hemp plant.

9. The genetically modified *Cannabis sativa* or hemp plant or part thereof of claim 6 wherein said heterologous polynucleotide sequence according to SEQ ID NO. 7 encodes a heterologous polypeptide according to the amino acid sequence SEQ ID NO. 6 or a fragment thereof wherein expression of the polynucleotide upregulates trichome formation.

10. The genetically modified *Cannabis sativa* or hemp plant or part thereof and its progeny of claim 9 wherein said nucleotide sequence according to SEQ ID NO. 7 that has been codon optimized for expression in *Cannabis sativa* or hemp.

11. A method of increasing cannabinoid formation in a plant comprising the steps:
stably transforming a *Cannabis* plant to express a heterologous polynucleotide sequence according to SEQ ID NO. 7, or a fragment thereof.

12. The method of claim 11 wherein said *Cannabis* plant is *Cannabis sativa* or hemp.

13. The method of claim 12 wherein the nucleotide sequence SEQ ID NO. 7 is operably linked to a promoter to produce an expression vector and wherein said expression vector is configured to be introduced via transformation to a *Cannabis sativa* or hemp plant.

14. A genetically modified *Cannabis sativa* or hemp plant or part thereof produced by the method of claim 13.

15. A genetically modified *Cannabis sativa* or hemp plant or part thereof produced by the method of claim 12.

16. The genetically modified *Cannabis sativa* or hemp plant or part thereof and its progeny of claim 15 wherein said plant or parts thereof and its progeny express the amino sequence according to SEQ ID NO. 6, or a fragment thereof, wherein expression of the polynucleotide upregulates formation of CBDA and/or THCA.

17. The genetically modified *Cannabis sativa* or hemp plant or part thereof and its progeny of claim 16 wherein the plant produces 4-fold the amount of THCA compared to a wild-type plant, 3-fold the amount of CBDA compared to a wild-type plant, and 30% more trichome structures compared to a wild-type plant.

18. The genetically modified *Cannabis sativa* or hemp plant or part thereof of claim 15 wherein its progeny is a seed from the genetically modified *Cannabis sativa* or hemp plant.

19. The genetically modified *Cannabis sativa* or hemp plant or part thereof and its progeny of claim 15 wherein said nucleotide sequence according to SEQ ID NO. 7 that has been codon optimized for expression in *Cannabis sativa* or hemp.

20. A method of increasing trichome formation in a plant comprising the steps:

stably transforming a *Cannabis* plant to express a heterologous polynucleotide sequence encoding transcription factor MYB1 from *Artemisia annua*, or a fragment thereof.

21. The method of claim 20, wherein said heterologous polynucleotide sequence encoding transcription factor MYB1 from *Artemisia annua* comprises a heterologous polynucleotide according to SEQ ID NO. 7, or a fragment thereof, that has been codon optimized for expression in *Cannabis sativa* or hemp.

22. The method of claim 21 wherein said *Cannabis* plant is *Cannabis sativa* or hemp.

23. The method of claim 22 wherein the nucleotide sequence SEQ ID NO. 7 is operably linked to a promoter to produce an expression vector and wherein said expression vector is configured to be introduced via transformation to a *Cannabis sativa* or hemp plant.

24. A genetically modified *Cannabis sativa* or hemp plant or part thereof produced by the method of claim 23.

25. The genetically modified *Cannabis sativa* or hemp plant or part thereof and its progeny of claim 22 wherein the plant produces 30% more trichome structures compared to a wild-type *Cannabis sativa* or hemp plant.

* * * * *

SEQUENCE LISTING

<160> NUMBER OF SEQ ID NOS: 14

<210> SEQ ID NO 1
<211> LENGTH: 1074
<212> TYPE: DNA
<213> ORGANISM: Cannabis

<400> SEQUENCE: 1

```
atgaagaaga acaaatcaac tagtaataat aagaacaaca acagtaataa tatcatcaaa      60
aacgacatcg tatcatcatc atcatcaaca acaacaacat catcaacaac tacagcaaca     120
tcatcatttc ataatgagaa agttactgtc agtactgatc atattattaa tcttgatgat     180
aagcagaaac gacaattatg tcgttgtcgt ttagaaaaag aagaagaaga agaaggaagt     240
ggtggttgtg gtgagacagt agtaatgatg ctagggtcag tatctcctgc tgctgctact     300
gctgctgcag ctgggggctc atcaagttgt gatgaagaca tgttgggtgg tcatgatcaa     360
ctgttgttgt tgtgttgttc tgagaaaaaa acgacagaaa tttcatcagt ggtgaacttt     420
aataataata ataataataa taaggaaaat ggtgacgaag tttcaggacc gtacgattat     480
catcatcata agaagaggag agaagaagaa gaagaagatg aagcatctgc atcagtagca     540
gctgttgatg aagggatgtt gttgtgcttt gatgacataa tagatagcca cttgctaaat     600
ccaaatgagg ttttgacttt aagagaagat agccataatg aaggtggggc agctgatcag     660
attgacaaga ctacttgtaa taatactact attactacta atgatgatta taacaataac     720
ttgatgatgt tgagctgcaa taataacgga gattatgtta ttagtgatga tcatgatgat     780
cagtactgga tagacgacgt cgttggagtt gactttttgga gttgggagag ttcgactact     840
actgttatta cccaagaaca agaacaagaa caagatcaag ttcaagaaca gaagaatatg     900
tgggataatg agaagagaaa actgttgtct ttgctatggg ataatagtga taacagcagc     960
agttgggagt tacaagataa aagcaataat aataataata ataatgttcc taacaaatgt    1020
```
caagagatta cctctgataa agaaaatgct atggttgcat ggcttctctc ctga    1074

<210> SEQ ID NO 2
<211> LENGTH: 357
<212> TYPE: PRT
<213> ORGANISM: Cannabis
<400> SEQUENCE: 2

```
Met Lys Lys Asn Lys Ser Thr Ser Asn Asn Lys Asn Asn Ser Asn
1               5                   10                  15

Asn Ile Ile Lys Asn Asp Ile Val Ser Ser Ser Ser Thr Thr Thr
                20                  25                  30

Thr Ser Ser Thr Thr Thr Ala Thr Ser Ser Phe His Asn Glu Lys Val
        35                  40                  45

Thr Val Ser Thr Asp His Ile Ile Asn Leu Asp Asp Lys Gln Lys Arg
    50                  55                  60

Gln Leu Cys Arg Cys Arg Leu Glu Lys Glu Glu Glu Glu Glu Gly Ser
65                  70                  75                  80

Gly Gly Cys Gly Glu Thr Val Val Met Met Leu Gly Ser Val Ser Pro
                85                  90                  95

Ala Ala Ala Thr Ala Ala Ala Gly Gly Ser Ser Ser Cys Asp Glu
                100                 105                 110

Asp Met Leu Gly Gly His Asp Gln Leu Leu Leu Cys Cys Ser Glu
                115                 120                 125

Lys Lys Thr Thr Glu Ile Ser Ser Val Val Asn Phe Asn Asn Asn Asn
                130                 135                 140

Asn Asn Asn Lys Glu Asn Gly Asp Glu Val Ser Gly Pro Tyr Asp Tyr
145                 150                 155                 160

His His His Lys Glu Glu Glu Glu Glu Glu Glu Asp Glu Ala Ser
                165                 170                 175

Ala Ser Val Ala Ala Val Asp Glu Gly Met Leu Leu Cys Phe Asp Asp
                180                 185                 190

Ile Ile Asp Ser His Leu Leu Asn Pro Asn Glu Val Leu Thr Leu Arg
                195                 200                 205

Glu Asp Ser His Asn Glu Gly Gly Ala Ala Asp Gln Ile Asp Lys Thr
    210                 215                 220

Thr Cys Asn Asn Thr Thr Ile Thr Thr Asn Asp Asp Tyr Asn Asn
225                 230                 235                 240

Leu Met Met Leu Ser Cys Asn Asn Asn Gly Asp Tyr Val Ile Ser Asp
                245                 250                 255

Asp His Asp Asp Gln Tyr Trp Ile Asp Val Val Gly Val Asp Phe
                260                 265                 270

Trp Ser Trp Glu Ser Ser Thr Thr Thr Val Ile Thr Gln Glu Gln Glu
                275                 280                 285

Gln Glu Gln Asp Gln Val Gln Glu Gln Lys Asn Met Trp Asp Asn Glu
    290                 295                 300

Lys Glu Lys Leu Leu Ser Leu Leu Trp Asp Asn Ser Asp Asn Ser Ser
305                 310                 315                 320

Ser Trp Glu Leu Gln Asp Lys Ser Asn Asn Asn Asn Asn Asn Val
                325                 330                 335

Pro Asn Lys Cys Gln Glu Ile Thr Ser Asp Lys Glu Asn Ala Met Val
                340                 345                 350

Ala Trp Leu Leu Ser
        355
```

```
<210> SEQ ID NO 3
<211> LENGTH: 462
<212> TYPE: PRT
<213> ORGANISM: Humulus lupulus

<400> SEQUENCE: 3

Met Gly Arg Ala Pro Cys Cys Glu Lys Val Gly Leu Lys Lys Gly Arg
1               5                   10                  15

Trp Thr Ser Glu Glu Asp Glu Ile Leu Thr Lys Tyr Ile Gln Ser Asn
            20                  25                  30

Gly Glu Gly Cys Trp Arg Ser Leu Pro Lys Asn Ala Gly Leu Leu Arg
        35                  40                  45

Cys Gly Lys Ser Cys Arg Leu Arg Trp Ile Asn Tyr Leu Arg Ala Asp
    50                  55                  60

Leu Lys Arg Gly Asn Ile Ser Ser Glu Glu Asp Ile Ile Ile Lys
65                  70                  75                  80

Leu His Ser Thr Leu Gly Asn Arg Trp Ser Leu Ile Ala Ser His Leu
                85                  90                  95

Pro Gly Arg Thr Asp Asn Glu Ile Lys Asn Tyr Trp Asn Ser His Leu
            100                 105                 110

Ser Arg Lys Ile His Thr Phe Arg Arg Cys Asn Asn Thr Thr His
        115                 120                 125

His His His Leu Pro Asn Leu Val Thr Val Thr Lys Val Asn Leu Pro
    130                 135                 140

Ile Pro Lys Arg Lys Gly Gly Arg Thr Ser Arg Leu Ala Met Lys Lys
145                 150                 155                 160

Asn Lys Ser Ser Thr Ser Asn Gln Asn Ser Ser Val Ile Lys Asn Asp
                165                 170                 175

Val Gly Ser Ser Ser Thr Thr Thr Ser Val His Gln Arg Thr
            180                 185                 190

Thr Thr Thr Thr Pro Thr Met Asp Asp Gln Gln Lys Arg Gln Leu Ser
            195                 200                 205

Arg Cys Arg Leu Glu Glu Lys Glu Asp Gln Asp Gly Ala Ser Thr Gly
        210                 215                 220

Thr Val Val Met Met Leu Gly Gln Ala Ala Ala Val Gly Ser Ser Cys
225                 230                 235                 240

Asp Glu Asp Met Leu Gly His Asp Gln Leu Ser Phe Leu Cys Cys Ser
                245                 250                 255

Glu Glu Lys Thr Thr Glu Asn Ser Met Thr Asn Leu Lys Glu Asn Gly
            260                 265                 270

Asp His Glu Val Ser Gly Pro Tyr Asp Tyr Asp His Arg Tyr Glu Lys
        275                 280                 285

Glu Thr Ser Val Asp Glu Gly Met Leu Leu Cys Phe Asn Asp Ile Ile
    290                 295                 300

Asp Ser Asn Leu Leu Asn Pro Asn Glu Val Leu Thr Leu Ser Glu Glu
305                 310                 315                 320

Ser Leu Asn Leu Gly Gly Ala Leu Met Asp Thr Thr Ser Thr Thr
                325                 330                 335

Thr Asn Asn Asn Asn Tyr Ser Leu Ser Tyr Asn Asn Gly Asp Cys
            340                 345                 350

Val Ile Ser Asp Asp His Asp Gln Tyr Trp Leu Asp Val Val Gly
        355                 360                 365

Val Asp Phe Trp Ser Trp Glu Ser Ser Thr Thr Val Thr Gln Glu Gln
    370                 375                 380
```

```
Glu Gln Glu Gln Glu Gln Glu Gln Glu Gln Glu Gln Glu Gln
385                 390                 395                 400

Glu Gln Glu His His His Gln Asp Gln Lys Lys Asn Thr Trp Asp
            405                 410                 415

Asn Glu Lys Glu Lys Met Leu Ala Leu Leu Trp Asp Ser Asp Asn Ser
            420                 425                 430

Asn Trp Glu Leu Gln Asp Asn Asn Tyr His Lys Cys Gln Glu Ile
        435                 440                 445

Thr Ser Asp Lys Glu Asn Ala Met Val Ala Trp Leu Leu Ser
    450                 455                 460
```

<210> SEQ ID NO 4
<211> LENGTH: 371
<212> TYPE: PRT
<213> ORGANISM: Arabidopsis thaliana

<400> SEQUENCE: 4

```
Met Gly Arg Ala Pro Cys Cys Glu Lys Val Gly Ile Lys Arg Gly Arg
1               5                   10                  15

Trp Thr Ala Glu Glu Asp Gln Ile Leu Ser Asn Tyr Ile Gln Ser Asn
            20                  25                  30

Gly Glu Gly Ser Trp Arg Ser Leu Pro Lys Asn Ala Gly Leu Lys Arg
        35                  40                  45

Cys Gly Lys Ser Cys Arg Leu Arg Trp Ile Asn Tyr Leu Arg Ser Asp
50                  55                  60

Leu Lys Arg Gly Asn Ile Thr Pro Glu Glu Glu Leu Val Val Lys
65                  70                  75                  80

Leu His Ser Thr Leu Gly Asn Arg Trp Ser Leu Ile Ala Gly His Leu
            85                  90                  95

Pro Gly Arg Thr Asp Asn Glu Ile Lys Asn Tyr Trp Asn Ser His Leu
        100                 105                 110

Ser Arg Lys Leu His Asn Phe Ile Arg Lys Pro Ser Ile Ser Gln Asp
    115                 120                 125

Val Ser Ala Val Ile Met Thr Asn Ala Ser Ser Ala Pro Pro Pro
130                 135                 140

Gln Ala Lys Arg Arg Leu Gly Arg Thr Ser Arg Ser Ala Met Lys Pro
145                 150                 155                 160

Lys Ile His Arg Thr Lys Thr Arg Lys Thr Lys Lys Thr Ser Ala Pro
            165                 170                 175

Pro Glu Pro Asn Ala Asp Val Ala Gly Ala Asp Lys Glu Ala Leu Met
        180                 185                 190

Val Glu Ser Ser Gly Ala Glu Ala Glu Leu Gly Arg Pro Cys Asp Tyr
    195                 200                 205

Tyr Gly Asp Asp Cys Asn Lys Asn Leu Met Ser Ile Asn Gly Asp Asn
210                 215                 220

Gly Val Leu Thr Phe Asp Asp Ile Ile Asp Leu Leu Leu Asp Glu
225                 230                 235                 240

Ser Asp Pro Gly His Leu Tyr Thr Asn Thr Thr Cys Gly Gly Asp Gly
            245                 250                 255

Glu Leu His Asn Ile Arg Asp Ser Glu Gly Ala Arg Gly Phe Ser Asp
        260                 265                 270

Thr Trp Asn Gln Gly Asn Leu Asp Cys Leu Leu Gln Ser Cys Pro Ser
    275                 280                 285

Val Glu Ser Phe Leu Asn Tyr Asp His Gln Val Asn Asp Ala Ser Thr
```

```
                290                 295                 300
Asp Glu Phe Ile Asp Trp Asp Cys Val Trp Gln Glu Gly Ser Asp Asn
305                 310                 315                 320

Asn Leu Trp His Glu Lys Glu Asn Pro Asp Ser Met Val Ser Trp Leu
            325                 330                 335

Leu Asp Gly Asp Asp Glu Ala Thr Ile Gly Asn Ser Asn Cys Glu Asn
        340                 345                 350

Phe Gly Glu Pro Leu Asp His Asp Asp Glu Ser Ala Leu Val Ala Trp
    355                 360                 365

Leu Leu Ser
    370

<210> SEQ ID NO 5
<211> LENGTH: 243
<212> TYPE: PRT
<213> ORGANISM: Arabidopsis thaliana

<400> SEQUENCE: 5

Met Asn Ile Ser Arg Thr Glu Phe Ala Asn Cys Lys Thr Leu Ile Asn
1               5                   10                  15

His Lys Glu Glu Val Glu Val Glu Lys Lys Met Glu Ile Glu Ile
            20                  25                  30

Arg Arg Gly Pro Trp Thr Val Glu Glu Asp Met Lys Leu Val Ser Tyr
        35                  40                  45

Ile Ser Leu His Gly Glu Gly Arg Trp Asn Ser Leu Ser Arg Ser Ala
    50                  55                  60

Gly Leu Asn Arg Thr Gly Lys Ser Cys Arg Leu Arg Trp Leu Asn Tyr
65                  70                  75                  80

Leu Arg Pro Asp Ile Arg Arg Gly Asp Ile Ser Leu Gln Glu Gln Phe
                85                  90                  95

Ile Ile Leu Glu Leu His Ser Arg Trp Gly Asn Arg Trp Ser Lys Ile
            100                 105                 110

Ala Gln His Leu Pro Gly Arg Thr Asp Asn Glu Ile Lys Asn Tyr Trp
        115                 120                 125

Arg Thr Arg Val Gln Lys His Ala Lys Leu Leu Lys Cys Asp Val Asn
    130                 135                 140

Ser Lys Gln Phe Lys Asp Thr Ile Lys His Leu Trp Met Pro Arg Leu
145                 150                 155                 160

Ile Glu Arg Ile Ala Ala Thr Gln Ser Val Gln Phe Thr Ser Asn His
                165                 170                 175

Tyr Ser Pro Glu Asn Ser Ser Val Ala Thr Ala Thr Ser Ser Thr Ser
            180                 185                 190

Ser Ser Glu Ala Val Arg Ser Ser Phe Tyr Gly Gly Asp Gln Val Glu
        195                 200                 205

Phe Gly Thr Leu Asp His Met Thr Asn Gly Gly Tyr Trp Phe Asn Gly
    210                 215                 220

Gly Asp Thr Phe Glu Thr Leu Cys Ser Phe Asp Glu Leu Asn Lys Trp
225                 230                 235                 240

Leu Ile Gln

<210> SEQ ID NO 6
<211> LENGTH: 330
<212> TYPE: PRT
<213> ORGANISM: Artemisia annua

<400> SEQUENCE: 6
```

Met Ala Arg His Ser Thr Cys Tyr Lys Gln Arg Leu Arg Lys Gly Leu
1               5                   10                  15

Trp Ser Pro Glu Glu Asp Glu Lys Leu Ile Lys His Ile Thr Lys Phe
            20                  25                  30

Gly His Gly Cys Trp Ser Ser Val Pro Lys Leu Ala Gly Leu Gln Arg
        35                  40                  45

Cys Gly Lys Ser Cys Arg Leu Arg Trp Ile Asn Tyr Leu Arg Pro Asp
    50                  55                  60

Leu Lys Arg Gly Thr Phe Ser Gln Gln Glu Thr Leu Ile Val Glu
65              70                  75                  80

Leu His Ala Val Leu Gly Asn Lys Trp Ser Gln Ile Ala Ala Gln Leu
                85                  90                  95

Pro Gly Arg Thr Asp Asn Glu Ile Lys Asn Leu Trp Asn Ser Ser Ile
            100                 105                 110

Lys Lys Lys Leu Arg Gln Arg Gly Ile Asp Pro Asn Thr His Lys Pro
        115                 120                 125

Leu Ser Asp Val Glu Asn Glu Asp Lys Pro Ser Pro Arg Ser Asn Asn
130             135                 140

Lys Asn His Gln Gln Thr Ile Ile Pro Ser Ile Glu Asn Pro Ser Leu
145                 150                 155                 160

Glu Thr His Glu Phe Phe Arg Asn Arg Phe Thr Thr Ser His Glu Asn
                165                 170                 175

Ala Asn Leu Ala Ser His Thr Asp Thr Lys His Asn Asn Thr Asp Gln
            180                 185                 190

Phe Ser Gly Phe Leu Asp Phe Ala Tyr Asn Gln Pro Pro Gln Pro Glu
        195                 200                 205

Ser Ser Leu Leu Phe Gly Ser Ser Ser Asn Thr Asp Thr Ser Leu Ser
210                 215                 220

Asn Pro Phe Gln Pro Thr Asn Trp Asp Thr Thr Thr Ser Leu Phe Asp
225                 230                 235                 240

Ala Asn Asn Gly Phe His Asn Gln Val Pro Leu Val Gly Asn Glu Ser
                245                 250                 255

Gln Pro Glu Asp Ile Lys Trp Asn Lys Tyr Leu Gln Ser Pro Phe Met
            260                 265                 270

Phe Gly Gly Ala Thr Leu Gln Ser Arg Val Leu Cys Asn Glu Thr Lys
        275                 280                 285

Pro Asp Leu Gly Met Ser Ile Asn Met Asn Met Asn Ile Asn Asn Glu
290                 295                 300

Leu Tyr Gly Asn His Glu Gly Val Asp Thr Tyr Asn Lys Gln Leu Gln
305                 310                 315                 320

Arg Ile Cys Ala Ser Tyr Gly Gln Phe Thr
                325                 330

<210> SEQ ID NO 7
<211> LENGTH: 993
<212> TYPE: DNA
<213> ORGANISM: Artemisia annua

<400> SEQUENCE: 7
atggctagac attcaacttg ctataaacaa agattgagaa aaggattgtg gtcacctgaa    60
gaagatgaaa aattgattaa acatattact aaatttggac atggatgctg gtcatcagtt   120
cctaaattgg ctggattgca agatgcggga aaatcatgca gattgagatg gattaattat   180
ttgagacctg atttgaaaag aggaactttt tcacaacaag aagaactttt gattgttgaa   240

```
ttgcatgctg ttttgggaaa taaatggtca caaattgctg ctcaattgcc tggaagaact        300
gataatgaaa ttaaaaattt gtggaattca tcaattaaaa aaaaattgag acaaagagga        360
attgatccta atactcataa acctttgtca gatgttgaaa atgaagataa accttcacct        420
agatcaaata ataaaaatca tcaacaaact attattcctt caattgaaaa tccttcattg        480
gaaactcatg aatttttttag aaatagattt actacttcac atgaaaatgc taatttggct        540
tcacatactg atactaaaca taataatact gatcaatttt caggattttt ggattttgct        600
tataatcaac ctcctcaacc tgaatcatca ttgttgtttg gatcatcatc aaatactgat        660
acttcattgt caaatccttt tcaacctact aattgggata ctactacttc attgtttgat        720
gctaataatg gatttcataa tcaagttcct ttggttggaa atgaatcaca acctgaagat        780
attaaatgga ataaatattt gcaatcacct tttatgtttg gaggagctac tttgcaatca        840
agagttttgt gcaatgaaac taaacctgat ttgggaatgt caattaatat gaatatgaat        900
attaataatg aattgtatgg aaatcatgaa ggagttgata cttataataa acaattgcaa        960
agaatttgcg cttcatatgg acaatttact taa                                    993
```

```
<210> SEQ ID NO 8
<211> LENGTH: 1392
<212> TYPE: DNA
<213> ORGANISM: Humulus lupulus

<400> SEQUENCE: 8
```

```
atgggaagag ctccttgctg cgaaaaagtt ggattgaaaa aaggaagatg gacttcagaa         60
gaagatgaaa ttttgactaa atatattcaa tcaaatggag aaggatgctg gagatcattg        120
cctaaaaatg ctggattgtt gagatgcgga aaatcatgca gattgagatg gattaattat        180
ttgagagctg atttgaaaag aggaaatatt tcatcagaag aagaagatat tattattaaa        240
ttgcattcaa ctttgggaaa tagatggtca ttgattgctt cacatttgcc tggaagaact        300
gataatgaaa ttaaaaatta ttggaattca catttgtcaa gaaaaattca tacttttaga        360
agatgcaata atactactac tcatcatcat catttgccta atttggttac tgttactaaa        420
gttaatttgc ctattcctaa aagaaaagga ggaagaactt caagattggc tatgaaaaaa        480
aataaatcat caacttcaaa tcaaaattca tcagttatta aaaatgatgt tggatcatca        540
tcatcaacta ctactacttc agttcatcaa agaactacta ctactactcc tactatggat        600
gatcaacaaa aaagacaatt gtcaagatgc agattggaag aaaaagaaga tcaagatgga        660
gcttcaactg gaactgttgt tatgatgttg gacaagctg ctgctgttgc tggatcatca        720
tgcgatgaag atatgttggg acatgatcaa ttgtcatttt tgtgctgctc agaagaaaaa        780
actactgaaa attcaatgac taatttgaaa gaaaatggag atcatgaagt ttcaggacct        840
tatgattatg atcatagata tgaaaaagaa acttcagttg atgaaggaat gttgttgtgc        900
tttaatgata ttattgattc aaatttgttg aatcctaatg aagtttttgac tttgtcagaa        960 gaatcattga atttgggagg agctttgatg gatactacta cttcaactac tactaataat       1020
aataattatt cattgtcata taataataat ggagattgcg ttatttcaga tgatcatgat       1080
caatattggt tggatgatgt tgttggagtt gattttttggt catgggaatc atcaactact       1140
gttactcaag aacaagaaca agaacaagaa caagaacaag aacaagaaca agaacaagaa       1200
caagaacaag aacatcatca tcaacaagat caaaaaaaaa atacttggga taatgaaaaa       1260
gaaaaaatgt tggctttgtt gtgggattca gataattcaa attgggaatt gcaagataat       1320
```
aataattatc ataaatgcca agaaattact tcagataaag aaaatgctat ggttgcttgg    1380
ttgttgtcat aa                                                        1392

<210> SEQ ID NO 9
<211> LENGTH: 1116
<212> TYPE: DNA
<213> ORGANISM: Arabidopsis thaliana

<400> SEQUENCE: 9
atgggaagag ctccttgctg cgaaaaagtt ggaattaaaa gaggaagatg gactgctgaa      60
gaagatcaaa ttttgtcaaa ttatattcaa tcaaatggag aaggatcatg gagatcattg     120
cctaaaaatg ctggattgaa agatgcggaa aaatcatgca gattgagatg gattaattat     180
ttgagatcag atttgaaaag aggaaatatt actcctgaag aagaagaatt ggttgttaaa     240
ttgcattcaa cttttgggaaa tagatggtca ttgattgctg acatttgcc tggaagaact     300 gataatgaaa ttaaaaatta ttggaattca catttgtcaa gaaaattgca taattttatt     360
agaaaacctt caatttcaca agatgtttca gctgttatta tgactaatgc ttcatcagct     420
cctcctcctc tcaagctaa aagaagattg ggaagaactt caagatcagc tatgaaacct     480
aaaattcata gaactaaaac tagaaaaact aaaaaaactt cagctcctcc tgaacctaat     540
gctgatgttg ctggagctga taagaagct tgatggttg aatcatcagg agctgaagct     600
gaattgggaa gaccttgcga ttattatgga tgatgattgca ataaaaattt gatgtcaatt     660
aatggagata atggagtttt gacttttgat gatgatatta ttgatttgtt gttggatgaa     720
tcagatcctg gacatttgta actaatact acttgcggag gagatggaga attgcataat     780
attagagatt cagaaggagc tagaggatttt tcagatactt ggaatcaagg aaatttggat     840
tgcttgttgc aatcatgccc ttcagttgaa tcattttga attatgatca tcaagttaat     900
gatgcttcaa ctgatgaatt tattgattgg gattgcgttt ggcaagaagg atcagataat     960
aatttgtggc atgaaaaaga aaatcctgat tcaatggttt catggttgtt ggatggagat    1020
gatgaagcta ctattggaaa ttcaaattgc gaaaattttg gagaacctt ggatcatgat    1080 gatgaatcag ctttggttgc ttggttgttg tcataa                             1116

<210> SEQ ID NO 10
<211> LENGTH: 352
<212> TYPE: PRT
<213> ORGANISM: Arabidopsis thaliana

<400> SEQUENCE: 10

Met Gly Arg His Ser Cys Cys Phe Lys Gln Lys Leu Arg Lys Gly Leu
1               5                   10                  15

Trp Ser Pro Glu Glu Asp Glu Lys Leu Leu Asn Tyr Ile Thr Arg His
            20                  25                  30

Gly His Gly Cys Trp Ser Ser Val Pro Lys Leu Ala Gly Leu Gln Arg
        35                  40                  45

Cys Gly Lys Ser Cys Arg Leu Arg Trp Ile Asn Tyr Leu Arg Pro Asp
    50                  55                  60

Leu Lys Arg Gly Ala Phe Ser Gln Asp Glu Glu Ser Leu Ile Ile Glu
65                  70                  75                  80

Leu His Ala Ala Leu Gly Asn Arg Trp Ser Gln Ile Ala Thr Arg Leu
                85                  90                  95

Pro Gly Arg Thr Asp Asn Glu Ile Lys Asn Phe Trp Asn Ser Cys Leu
            100                 105                 110

```
Lys Lys Lys Leu Arg Arg Lys Gly Ile Asp Pro Thr Thr His Lys Pro
            115                 120                 125

Leu Ile Thr Asn Glu Leu Gln Ser Leu Asn Val Ile Asp Gln Lys Leu
    130                 135                 140

Thr Ser Ser Glu Val Val Lys Ser Thr Gly Ser Ile Asn Asn Leu His
145                 150                 155                 160

Asp Gln Ser Met Val Val Ser Ser Gln Gln Gly Pro Trp Trp Phe Pro
                165                 170                 175

Ala Asn Thr Thr Thr Asn Gln Asn Ser Ala Phe Cys Phe Ser Ser
                180                 185                 190

Ser Asn Thr Thr Thr Val Ser Asp Gln Ile Val Ser Leu Ile Ser Ser
                195                 200                 205

Met Ser Thr Ser Ser Ser Pro Thr Pro Met Thr Ser Asn Phe Ser Pro
    210                 215                 220

Ala Pro Asn Asn Trp Glu Gln Leu Asn Tyr Cys Asn Thr Val Pro Ser
225                 230                 235                 240

Gln Ser Asn Ser Ile Tyr Ser Ala Phe Phe Gly Asn Gln Tyr Thr Glu
                245                 250                 255

Ala Ser Gln Thr Met Asn Asn Asn Asn Pro Leu Val Asp Gln His His
                260                 265                 270

His His Gln Asp Met Lys Ser Trp Ala Ser Glu Ile Leu His Tyr Thr
        275                 280                 285

Glu His Asn Gln Ser Ser Glu Thr Val Ile Glu Ala Glu Val Lys Pro
    290                 295                 300

Asp Ile Ala Asn Tyr Tyr Trp Arg Ser Ala Ser Ser Ser Ser Pro
305                 310                 315                 320

Asn Gln Glu Ala Ala Thr Leu Leu His Asp Ala Asn Val Glu Val Tyr
                325                 330                 335

Gly Lys Asn Leu Gln Lys Leu Asn Asn Met Val Phe Asp Gln Ser Leu
                340                 345                 350

<210> SEQ ID NO 11
<211> LENGTH: 348
<212> TYPE: PRT
<213> ORGANISM: Arabidopsis thaliana

<400> SEQUENCE: 11

Met Gly Arg His Ser Cys Cys Tyr Lys Gln Lys Leu Arg Lys Gly Leu
1               5                   10                  15

Trp Ser Pro Glu Glu Asp Glu Lys Leu Leu Arg Tyr Ile Thr Lys Tyr
                20                  25                  30

Gly His Gly Cys Trp Ser Ser Val Pro Lys Gln Ala Gly Thr Phe Leu
            35                  40                  45

Phe Ile Gln Ile His Leu Leu Phe Gly Leu Gln Arg Cys Gly Lys Ser
    50                  55                  60

Cys Arg Leu Arg Trp Ile Asn Tyr Leu Arg Pro Asp Leu Lys Arg Gly
65                  70                  75                  80

Ala Phe Ser Gln Asp Glu Glu Asn Leu Ile Ile Glu Leu His Ala Val
                85                  90                  95

Leu Gly Asn Arg Trp Ser Gln Ile Ala Ala Gln Leu Pro Gly Arg Thr
            100                 105                 110

Asp Asn Glu Ile Lys Asn Leu Trp Asn Ser Cys Leu Lys Lys Lys Leu
        115                 120                 125

Arg Leu Arg Gly Ile Asp Pro Val Thr His Lys Leu Leu Thr Glu Ile
    130                 135                 140
```

Glu Thr Gly Thr Asp Asp Lys Thr Lys Pro Val Glu Lys Ser Gln Gln
145                 150                 155                 160

Thr Tyr Leu Val Glu Thr Asp Gly Ser Ser Thr Thr Cys Ser
                165                 170                 175

Thr Asn Gln Asn Asn Thr Asp His Leu Tyr Thr Gly Asn Phe Gly
            180                 185                 190

Phe Gln Arg Leu Ser Leu Glu Asn Gly Ser Arg Ile Ala Ala Gly Ser
        195                 200                 205

Asp Leu Gly Ile Trp Ile Pro Gln Thr Gly Arg Asn His His His
        210                 215                 220

Val Asp Glu Thr Ile Pro Ser Ala Val Val Leu Pro Gly Ser Met Phe
225                 230                 235                 240

Ser Ser Gly Leu Thr Gly Tyr Arg Ser Ser Asn Leu Gly Leu Ile Glu
                245                 250                 255

Leu Glu Asn Ser Phe Ser Thr Gly Pro Met Met Thr Glu His Gln Gln
            260                 265                 270

Ile Gln Glu Ser Asn Tyr Asn Asn Ser Thr Phe Phe Gly Asn Gly Asn
        275                 280                 285

Leu Asn Trp Gly Leu Thr Met Glu Glu Asn Gln Asn Pro Phe Thr Ile
290                 295                 300

Ser Asn His Ser Asn Ser Ser Leu Tyr Ser Asp Ile Lys Ser Glu Thr
305                 310                 315                 320

Asn Phe Phe Gly Thr Glu Ala Thr Asn Val Gly Met Trp Pro Cys Asn
                325                 330                 335

Gln Leu Gln Pro Gln Gln His Ala Tyr Gly His Ile
            340                 345

<210> SEQ ID NO 12
<211> LENGTH: 366
<212> TYPE: PRT
<213> ORGANISM: Arabidopsis thaliana

<400> SEQUENCE: 12

Met Gly Arg His Ser Cys Cys Tyr Lys Gln Lys Leu Arg Lys Gly Leu
1               5                   10                  15

Trp Ser Pro Glu Glu Asp Glu Lys Leu Leu Thr His Ile Thr Asn His
                20                  25                  30

Gly His Gly Cys Trp Ser Ser Val Pro Lys Leu Ala Gly Leu Gln Arg
            35                  40                  45

Cys Gly Lys Ser Cys Arg Leu Arg Trp Ile Asn Tyr Leu Arg Pro Asp
        50                  55                  60

Leu Lys Arg Gly Ala Phe Ser Pro Glu Glu Asn Leu Ile Val Glu
65                  70                  75                  80

Leu His Ala Val Leu Gly Asn Arg Trp Ser Gln Ile Ala Ser Arg Leu
                85                  90                  95

Pro Gly Arg Thr Asp Asn Glu Ile Lys Asn Leu Trp Asn Ser Ser Ile
            100                 105                 110

Lys Lys Lys Leu Lys Gln Arg Gly Ile Asp Pro Asn Thr His Lys Pro
        115                 120                 125

Ile Ser Glu Val Glu Ser Phe Ser Asp Lys Asp Lys Pro Thr Thr Ser
    130                 135                 140

Asn Asn Lys Arg Ser Gly Asn Asp His Lys Ser Pro Ser Ser Ser Ser
145                 150                 155                 160

Ala Thr Asn Gln Asp Phe Phe Leu Glu Arg Pro Ser Asp Leu Ser Asp

```
                         165                 170                 175
Tyr Phe Gly Phe Gln Lys Leu Asn Phe Asn Ser Asn Leu Gly Leu Ser
                180                 185                 190

Val Thr Thr Asp Ser Ser Leu Cys Ser Met Ile Pro Pro Gln Phe Ser
            195                 200                 205

Pro Gly Asn Met Val Gly Ser Val Leu Gln Thr Pro Val Cys Val Lys
        210                 215                 220

Pro Ser Ile Ser Leu Pro Pro Asp Asn Ser Ser Ser Pro Ile Ser
225                 230                 235                 240

Gly Gly Asp His Val Lys Leu Ala Ala Pro Asn Trp Glu Phe Gln Thr
                245                 250                 255

Asn Asn Asn Asn Thr Ser Asn Phe Phe Asp Asn Gly Gly Phe Ser Trp
                260                 265                 270

Ser Ile Pro Asn Ser Ser Thr Ser Ser Ser Gln Val Lys Pro Asn His
                275                 280                 285

Asn Phe Glu Glu Ile Lys Trp Ser Glu Tyr Leu Asn Thr Pro Phe Phe
                290                 295                 300

Ile Gly Ser Thr Val Gln Ser Gln Thr Ser Gln Pro Ile Tyr Ile Lys
305                 310                 315                 320

Ser Glu Thr Asp Tyr Leu Ala Asn Val Ser Asn Met Thr Asp Pro Trp
                325                 330                 335

Ser Gln Asn Glu Asn Leu Gly Thr Thr Glu Thr Ser Asp Val Phe Ser
                340                 345                 350

Lys Asp Leu Gln Arg Met Ala Val Ser Phe Gly Gln Ser Leu
                355                 360                 365

<210> SEQ ID NO 13
<211> LENGTH: 314
<212> TYPE: PRT
<213> ORGANISM: Arabidopsis thaliana

<400> SEQUENCE: 13

Met Lys Arg His Ser Cys Cys Tyr Lys Gln Lys Leu Arg Lys Gly Leu
1               5                   10                  15

Trp Ser Pro Glu Glu Asp Glu Lys Leu Leu Asn Tyr Ile Thr Lys His
                20                  25                  30

Gly His Gly Cys Trp Ser Ser Val Pro Lys Leu Ala Gly Leu Glu Arg
            35                  40                  45

Cys Gly Lys Ser Cys Arg Leu Arg Trp Ile Asn Tyr Leu Arg Pro Asp
        50                  55                  60

Leu Lys Arg Gly Ala Phe Ser Glu Glu Gln Asn Leu Ile Val Glu
65                  70                  75                  80

Leu His Ala Val Leu Gly Asn Arg Trp Ser Gln Ile Ala Ala Arg Leu
                85                  90                  95

Pro Gly Arg Thr Asp Asn Glu Ile Lys Asn Leu Trp Asn Ser Cys Ile
            100                 105                 110

Lys Lys Lys Leu Met Lys Lys Gly Ile Asp Pro Ile Thr His Lys Pro
        115                 120                 125

Leu Ser Glu Val Gly Lys Glu Thr Asn Arg Ser Asp Asn Asn Ser
    130                 135                 140

Thr Ser Phe Ser Ser Glu Thr Asn Gln Asp Leu Phe Val Lys Lys Thr
145                 150                 155                 160

Ser Asp Phe Ala Glu Tyr Ser Ala Phe Gln Lys Glu Ser Asn Ser
                165                 170                 175
```

```
Val Ser Leu Arg Asn Ser Leu Ser Ser Met Ile Pro Thr Gln Phe Asn
            180                 185                 190

Ile Asp Asp Gly Ser Val Ser Asn Ala Gly Phe Asp Thr Gln Val Cys
        195                 200                 205

Val Lys Pro Ser Ile Ile Leu Leu Pro Pro Pro Asn Asn Thr Ser Ser
        210                 215                 220

Thr Val Ser Gly Gln Asp His Val Asn Val Ser Glu Pro Asn Trp Glu
225                 230                 235                 240

Ser Asn Ser Gly Thr Thr Ser His Leu Asn Asn Pro Gly Met Glu Glu
                245                 250                 255

Met Lys Trp Ser Glu Glu Tyr Leu Asn Glu Ser Leu Phe Ser Thr Gln
            260                 265                 270

Val Tyr Val Lys Ser Glu Thr Asp Phe Asn Ser Asn Ile Ala Phe Pro
        275                 280                 285

Trp Ser Gln Ser Gln Ala Cys Asp Val Phe Pro Lys Asp Leu Gln Arg
        290                 295                 300

Met Ala Phe Ser Phe Gly Gly Gln Thr Leu
305                 310

<210> SEQ ID NO 14
<211> LENGTH: 463
<212> TYPE: PRT
<213> ORGANISM: Humulus lupulus

<400> SEQUENCE: 14

Met Gly Arg Ala Pro Cys Cys Glu Lys Val Gly Leu Lys Lys Gly Arg
1               5                   10                  15

Trp Thr Ser Glu Glu Asp Glu Ile Leu Thr Lys Tyr Ile Gln Ser Asn
            20                  25                  30

Gly Glu Gly Cys Trp Arg Ser Leu Pro Lys Asn Ala Gly Leu Leu Arg
        35                  40                  45

Cys Gly Lys Ser Cys Arg Leu Arg Trp Ile Asn Tyr Leu Arg Ala Asp
    50                  55                  60

Leu Lys Arg Gly Asn Ile Ser Ser Glu Glu Asp Ile Ile Ile Lys
65                  70                  75                  80

Leu His Ser Thr Leu Gly Asn Arg Trp Ser Leu Ile Ala Ser His Leu
                85                  90                  95

Pro Gly Arg Thr Asp Asn Glu Ile Lys Asn Tyr Trp Asn Ser His Leu
            100                 105                 110

Ser Arg Lys Ile His Thr Phe Arg Arg Cys Asn Asn Thr Thr Thr His
        115                 120                 125

His His His Leu Pro Asn Leu Val Thr Val Thr Lys Val Asn Leu Pro
    130                 135                 140

Ile Pro Lys Arg Lys Gly Gly Arg Thr Ser Arg Leu Ala Met Lys Lys
145                 150                 155                 160

Asn Lys Ser Ser Thr Ser Asn Gln Asn Ser Ser Val Ile Lys Asn Asp
                165                 170                 175

Val Gly Ser Ser Ser Ser Thr Thr Thr Thr Ser Val His Gln Arg Thr
            180                 185                 190

Thr Thr Thr Thr Pro Thr Met Asp Asp Gln Gln Lys Arg Gln Leu Ser
        195                 200                 205

Arg Cys Arg Leu Glu Glu Lys Glu Asp Gln Asp Gly Ala Ser Thr Gly
    210                 215                 220

Thr Val Val Met Met Leu Gly Gln Ala Ala Ala Val Ala Gly Ser Ser
225                 230                 235                 240
```

```
Cys Asp Glu Asp Met Leu Gly His Asp Gln Leu Ser Phe Leu Cys Cys
                245                 250                 255

Ser Glu Glu Lys Thr Thr Glu Asn Ser Met Thr Asn Leu Lys Glu Asn
            260                 265                 270

Gly Asp His Glu Val Ser Gly Pro Tyr Asp Tyr Asp His Arg Tyr Glu
        275                 280                 285

Lys Glu Thr Ser Val Asp Glu Gly Met Leu Leu Cys Phe Asn Asp Ile
    290                 295                 300

Ile Asp Ser Asn Leu Leu Asn Pro Asn Glu Val Leu Thr Leu Ser Glu
305                 310                 315                 320

Glu Ser Leu Asn Leu Gly Gly Ala Leu Met Asp Thr Thr Thr Ser Thr
                325                 330                 335

Thr Thr Asn Asn Asn Asn Tyr Ser Leu Ser Tyr Asn Asn Asn Gly Asp
            340                 345                 350

Cys Val Ile Ser Asp Asp His Asp Gln Tyr Trp Leu Asp Asp Val Val
            355                 360                 365

Gly Val Asp Phe Trp Ser Trp Glu Ser Ser Thr Thr Val Thr Gln Glu
    370                 375                 380

Gln Glu Gln Glu Gln Glu Gln Glu Gln Glu Gln Glu Gln Glu Gln Glu
385                 390                 395                 400

Gln Glu Gln Glu His His His Gln Gln Asp Gln Lys Lys Asn Thr Trp
            405                 410                 415

Asp Asn Glu Lys Glu Lys Met Leu Ala Leu Leu Trp Asp Ser Asp Asn
            420                 425                 430

Ser Asn Trp Glu Leu Gln Asp Asn Asn Asn Tyr His Lys Cys Gln Glu
        435                 440                 445

Ile Thr Ser Asp Lys Glu Asn Ala Met Val Ala Trp Leu Leu Ser
    450                 455                 460
```